(12) United States Patent
Slayton et al.

(10) Patent No.: US 7,530,356 B2
(45) Date of Patent: May 12, 2009

(54) METHOD AND SYSTEM FOR NONINVASIVE MASTOPEXY

(75) Inventors: Michael H. Slayton, Tempe, AZ (US); Peter G. Barthe, Phoenix, AZ (US); Inder Raj S. Makin, Mesa, AZ (US)

(73) Assignee: Guided Therapy Systems, Inc., Mesa, AZ (US)

( * ) Notice: Subject to any disclaimer, the term of this patent is extended or adjusted under 35 U.S.C. 154(b) by 519 days.

(21) Appl. No.: 11/163,155

(22) Filed: Oct. 6, 2005

(65) Prior Publication Data

US 2006/0074314 A1    Apr. 6, 2006

Related U.S. Application Data

(60) Provisional application No. 60/616,355, filed on Oct. 6, 2004.

(51) Int. Cl.
*A61B 8/00* (2006.01)
*A61B 18/04* (2006.01)

(52) U.S. Cl. .............. 128/898; 606/27; 600/439; 607/96

(58) Field of Classification Search ............ 606/27, 606/41, 49–50; 607/96, 115; 600/439; 128/898
See application file for complete search history.

(56) References Cited

U.S. PATENT DOCUMENTS

| 4,372,296 A | 2/1983 | Fahim |
| 4,528,979 A | 7/1985 | Marchenko et al. |
| 5,115,814 A | 5/1992 | Griffith et al. |
| 5,419,327 A | 5/1995 | Rohwedder et al. |
| 5,524,620 A | 6/1996 | Rosenschein et al. |
| 5,558,092 A | 9/1996 | Unger |
| 5,658,328 A * | 8/1997 | Johnson .............. 623/8 |
| 5,660,836 A | 8/1997 | Knowlton |
| 5,665,053 A | 9/1997 | Jacobs |
| 5,690,608 A | 11/1997 | Watanabe et al. |
| 5,755,753 A | 5/1998 | Knowlton |
| 5,817,021 A | 10/1998 | Reichenberger |
| 5,871,524 A | 2/1999 | Knowlton |
| 5,919,219 A | 7/1999 | Knowlton |
| 5,938,612 A | 8/1999 | Kline-Schoder |
| 5,948,011 A | 9/1999 | Knowlton |

(Continued)

FOREIGN PATENT DOCUMENTS

EP    1234566    8/2002

(Continued)

*Primary Examiner*—Michael Peffley
*Assistant Examiner*—Alex Helmboldt
(74) *Attorney, Agent, or Firm*—Snell & Wilmer LLP

(57) ABSTRACT

Methods and systems for noninvasive mastopexy through deep tissue tightening with ultrasound are provided. An exemplary method and system comprise a therapeutic ultrasound system configured for providing ultrasound treatment to a deep tissue region, such as a region comprising muscular fascia and ligaments. In accordance with various exemplary embodiments, a therapeutic ultrasound system can be configured to achieve depth from 1 mm to 4 cm with a conformal selective deposition of ultrasound energy without damaging an intervening tissue in the range of frequencies from 1 to 15 MHz. In addition, a therapeutic ultrasound can also be configured in combination with ultrasound imaging or imaging/monitoring capabilities, either separately configured with imaging, therapy and monitoring systems or any level of integration thereof.

17 Claims, 18 Drawing Sheets

U.S. PATENT DOCUMENTS

| | | | |
|---|---|---|---|
| 5,968,034 A | 10/1999 | Fullmer et al. |
| 6,039,048 A | 3/2000 | Silberg |
| 6,071,239 A | 6/2000 | Cribbs et al. |
| 6,090,054 A | 7/2000 | Tagishi et al. |
| 6,093,883 A | 7/2000 | Sanghvi et al. |
| 6,113,559 A | 9/2000 | Klopotek |
| 6,176,840 B1 | 1/2001 | Nishimura et al. |
| 6,183,426 B1 | 2/2001 | Akisada et al. |
| 6,183,502 B1 | 2/2001 | Takeuchi |
| 6,183,773 B1 | 2/2001 | Anderson |
| 6,190,336 B1 | 2/2001 | Duarte et al. |
| 6,241,753 B1 | 6/2001 | Knowlton |
| 6,273,864 B1 | 8/2001 | Duarte et al. |
| 6,311,090 B1 | 10/2001 | Knowlton |
| 6,315,741 B1 | 11/2001 | Martin et al. |
| 6,325,769 B1 | 12/2001 | Klopotek |
| 6,350,276 B1 | 2/2002 | Knowlton |
| 6,361,531 B1 | 3/2002 | Hissong |
| 6,375,672 B1 | 4/2002 | Aksan et al. |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,405,090 B1 | 6/2002 | Knowlton |
| 6,409,720 B1 | 6/2002 | Hissong |
| 6,413,253 B1 | 7/2002 | Koop et al. |
| 6,413,254 B1 | 7/2002 | Hissong et al. |
| 6,419,648 B1 | 7/2002 | Vitek et al. |
| 6,425,912 B1 | 7/2002 | Knowlton |
| 6,428,532 B1 | 8/2002 | Doukas et al. |
| 6,430,446 B1 | 8/2002 | Knowlton |
| 6,432,101 B1 | 8/2002 | Weber et al. |
| 6,436,061 B1 | 8/2002 | Costantino |
| 6,438,424 B1 | 8/2002 | Knowlton |
| 6,440,121 B1 | 8/2002 | Weber et al. |
| 6,443,914 B1 | 9/2002 | Costantino |
| 6,461,378 B1 | 10/2002 | Knowlton |
| 6,470,216 B1 | 10/2002 | Knowlton |
| 6,500,121 B1 | 12/2002 | Slayton et al. |
| 6,500,141 B1 | 12/2002 | Irion et al. |
| 6,511,428 B1 | 1/2003 | Azuma et al. |
| 6,595,934 B1 | 7/2003 | Hissong et al. |
| 6,607,498 B2 | 8/2003 | Eshel |
| 6,623,430 B1 | 9/2003 | Slayton et al. |
| 6,626,854 B2 | 9/2003 | Friedman et al. |
| 6,685,640 B1 | 2/2004 | Fry et al. |
| 6,692,450 B1 | 2/2004 | Coleman |
| 6,699,237 B2 | 3/2004 | Weber et al. |
| 6,932,771 B2 | 8/2005 | Whitmore et al. |
| 6,936,046 B2 | 8/2005 | Hissong et al. |
| 6,976,492 B2 * | 12/2005 | Ingle et al. ............... 128/898 |
| 7,006,874 B2 | 2/2006 | Knowlton |
| 7,020,528 B2 | 3/2006 | Neev |
| 7,022,089 B2 | 4/2006 | Ooba et al. |
| 7,063,666 B2 | 6/2006 | Weng et al. |
| 7,115,123 B2 | 10/2006 | Knowlton et al. |
| 7,189,230 B2 | 3/2007 | Knowlton |
| 7,258,674 B2 * | 8/2007 | Cribbs et al. ............... 601/2 |
| 7,347,855 B2 | 3/2008 | Eshel et al. |
| 2002/0040199 A1 | 4/2002 | Klopotek |
| 2002/0055702 A1 | 5/2002 | Atala et al. |
| 2002/0082528 A1 | 6/2002 | Friedman et al. |
| 2002/0082589 A1 | 6/2002 | Friedman et al. |
| 2002/0161357 A1 | 10/2002 | Anderson et al. |
| 2002/0169442 A1 | 11/2002 | Neev |
| 2002/0193831 A1 | 12/2002 | Smith |
| 2003/0032900 A1 | 2/2003 | Ella |
| 2003/0036706 A1 | 2/2003 | Slayton et al. |
| 2003/0040739 A1 | 2/2003 | Koop |
| 2003/0050678 A1 | 3/2003 | Sierra et al. |
| 2003/0074023 A1 * | 4/2003 | Kaplan et al. ............... 606/228 |
| 2003/0083536 A1 | 5/2003 | Eshel et al. |
| 2003/0176790 A1 | 9/2003 | Slayton et al. |
| 2003/0212351 A1 | 11/2003 | Hissong et al. |
| 2003/0212393 A1 | 11/2003 | Knowlton et al. |
| 2003/0216795 A1 | 11/2003 | Harth et al. |
| 2003/0236487 A1 | 12/2003 | Knowlton |
| 2004/0000316 A1 | 1/2004 | Knowlton et al. |
| 2004/0001809 A1 | 1/2004 | Brisken et al. |
| 2004/0002705 A1 | 1/2004 | Knowlton et al. |
| 2004/0015106 A1 | 1/2004 | Coleman |
| 2004/0030227 A1 * | 2/2004 | Littrup et al. ............... 600/300 |
| 2004/0186535 A1 | 9/2004 | Knowlton et al. |
| 2004/0206365 A1 | 10/2004 | Knowlton |
| 2005/0055073 A1 | 3/2005 | Weber |
| 2005/0154332 A1 | 7/2005 | Zanelli et al. |
| 2005/0261584 A1 | 11/2005 | Eshel et al. |
| 2006/0074313 A1 | 4/2006 | Slayton et al. |
| 2006/0079868 A1 | 4/2006 | Makin et al. |
| 2006/0089632 A1 | 4/2006 | Barthe et al. |
| 2006/0089688 A1 | 4/2006 | Panescu |
| 2006/0111744 A1 | 5/2006 | Makin et al. |
| 2006/0116671 A1 | 6/2006 | Slayton et al. |
| 2006/0122508 A1 | 6/2006 | Slayton et al. |
| 2006/0122509 A1 | 6/2006 | Desilets |
| 2006/0241440 A1 | 10/2006 | Eshel et al. |
| 2006/0241442 A1 | 10/2006 | Barthe et al. |
| 2007/0032784 A1 | 2/2007 | Gliklich et al. |
| 2007/0055156 A1 | 3/2007 | Desilets et al. |

FOREIGN PATENT DOCUMENTS

| | | |
|---|---|---|
| JP | 3123559 | 5/1991 |
| JP | 4089058 | 3/1992 |
| JP | 7080087 | 3/1995 |
| JP | 7222782 | 8/1995 |
| WO | WO 9832379 | 7/1998 |
| WO | WO 9933520 | 7/1999 |
| WO | WO 0015300 | 3/2000 |
| WO | WO 0021612 | 4/2000 |
| WO | WO 02092168 | 11/2002 |
| WO | WO 03070105 | 8/2003 |
| WO | WO 03086215 | 10/2003 |

* cited by examiner

US 7,530,356 B2

METHOD AND SYSTEM FOR NONINVASIVE MASTOPEXY

CROSS-REFERENCE TO RELATED APPLICATIONS

This invention claims priority to and the benefit of U.S. Provisional No. 60/616,355, filed on Oct. 6, 2004, which is hereby incorporated by reference.

FIELD OF INVENTION

The present invention relates to ultrasound therapy systems, and in particular to a method and system for noninvasive mastopexy.

BACKGROUND OF INVENTION

Coarse sagging of the skin and facial musculature occurs gradually over time due to gravity and chronic changes in connective tissue associated with aging. Invasive surgical treatment to tighten such tissues is common, for example by face-lifts. In these treatments for connective tissue sagging, a portion of the tissue is usually removed, and sutures or other fasteners are used to suspend the sagging tissue structures. On the breasts, the muscular fascia and ligaments form a layer superficial to the muscles and beneath the skin and subcutaneous fat. Breast sagging is due to a process in which the suspensory (Cooper's) ligaments become lax. Surgical tightening of the underlying muscular fascia and ligaments is needed for surgical correction through a procedure referred to as mastopexy, or more commonly known as breast lifts.

Radio frequency (RF) devices have been used to produce heating and shrinkage of skin on the face and breast, with some success as a non-invasive alternative to surgical lifting procedures. However, RF is a dispersive form of energy deposition. It is impossible to control precisely the heated tissue volume and depth, because resistive heating of tissues by RF energy occurs along the entire path of electrical conduction through tissues. Another restriction of RF energy for non-invasive tightening of Cooper's ligaments is unwanted destruction of the overlying fat and skin layers. High impedance to RF within fat, overlying the suspensory connective structures intended for shrinking, leads to higher temperatures in the fat than in the target suspensory structures. Similarly, mid-infrared lasers and other light sources have been used as attempts to non-invasively heat and shrink connective tissues of the dermis. However, light is not capable of non-invasive treatment of Cooper's ligaments, because light does not penetrate deeply enough to produce local heating there. Below a depth of approximately 1 mm, light energy is multiply scattered and cannot be focused to achieve precise local heating.

SUMMARY OF INVENTION

In accordance with various aspects of the present invention, methods and systems for noninvasive breasts lifts through deep tissue tightening with ultrasound are provided. An exemplary method and system comprise a therapeutic ultrasound system configured for providing ultrasound treatment to a deep tissue region, such as a region comprising muscular fascia and ligaments.

In accordance with various exemplary embodiments, a therapeutic ultrasound system can be configured to achieve depth from 1 mm to 4 cm with a conformal selective deposition of ultrasound energy without damaging an intervening tissue in the range of frequencies from 1 to 15 MHz. In addition, a therapeutic ultrasound can also be configured in combination with ultrasound imaging or imaging/monitoring capabilities, either separately configured with imaging, therapy and monitoring systems or any level of integration thereof.

An exemplary therapeutic ultrasound system can also be substantially capable of conformal and localized deposition of ultrasound energy as well as targeting and/or monitoring capabilities. Further, a therapeutic ultrasound can also avoid heating, cavitation or other distractive events in the intervening tissue that contains vital structures, as well as tissue posterior to the conformal lesion to avoid the same.

BRIEF DESCRIPTION OF THE DRAWINGS

The subject matter of the invention is particularly pointed out in the concluding portion of the specification. The invention, however, both as to organization and method of operation, may best be understood by reference to the following description taken in conjunction with the accompanying drawing figures, in which like parts may be referred to by like numerals.

DETAILED DESCRIPTION

The present invention may be described herein in terms of various functional components and processing steps. It should be appreciated that such components and steps may be realized by any number of hardware components configured to perform the specified functions. For example, the present invention may employ various medical treatment devices, visual imaging and display devices, input terminals and the like, which may carry out a variety of functions under the control of one or more control systems or other control devices. In addition, the present invention may be practiced in any number of medical contexts and that the exemplary embodiments relating to noninvasive mastopexy therapy treatment systems, imaging systems and monitoring systems as described herein are merely indicative of exemplary applications for the invention. For example, the principles, features and methods discussed may be applied to any medical application. Further, various aspects of the present invention may be suitably applied to other applications.

Figure 1:
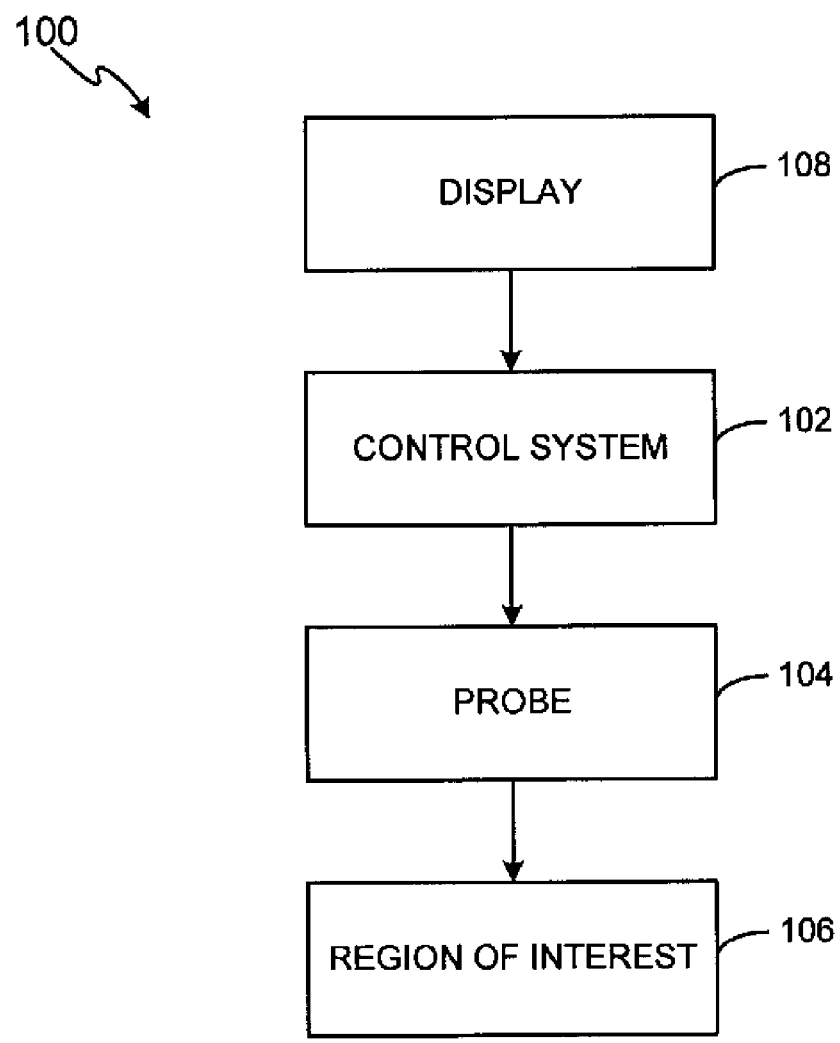
FIG. 1 illustrates a block diagram of an exemplary ultrasound treatment system for noninvasive mastopexy in accordance with an exemplary embodiment of the present invention.

In accordance with various aspects of the present invention, a method and system for noninvasive breasts lifts through deep tissue tightening with ultrasound are provided. For example, in accordance with an exemplary embodiment, with reference to FIG. 1, an exemplary treatment system 100 configured to treat a region of interest 106 comprises a control system 102, an imaging/therapy probe with acoustic coupling 104, and a display system 108.

Control system 102 and display system 108 can comprise various configurations for controlling probe 104 and overall system 100 functionality, such as, for example, a microprocessor with software and a plurality of input/output devices, system and devices for controlling electronic and/or mechanical scanning and/or multiplexing of transducers, a system for power delivery, systems for monitoring, systems for sensing the spatial position of the probe and/or transducers, and/or systems for handling user input and recording treatment results, among others. Imaging/therapy probe 104 can comprise various probe and/or transducer configurations. For example, probe 104 can be configured for a combined dual-mode imaging/therapy transducer, coupled or co-housed imaging/therapy transducers, or simply a separate therapy probe and an imaging probe.

In accordance with an exemplary embodiment, treatment system 100 is configured for treating the superficial layers of tissue of a breast, e.g., a deep tissue region, such as a region comprising muscular fascia, ligaments, Cooper's ligaments, suspensory ligaments, ligaments located underneath the breast tissue, and/or muscle, fat or dermis regions, by first, imaging of region of interest 106 for localization of the treatment area and surrounding structures, second, delivery of ultrasound energy at a depth, distribution, timing, and energy level to achieve the desired therapeutic effect, and third to monitor the treatment area before, during, and after therapy to plan and assess the results and/or provide feedback.

As to the treatment of the region comprising muscular fascia and ligaments, tissue can be permanently tightened by thermal ablation to temperatures about 60 degrees C. or higher resulting in the desired lifting of the breast.

In addition, the muscular fascia and ligaments region is typically about 1 mm to 4 cm deep, and varies in depth and thickness at different locations. Techniques for local heating of regions of the Cooper's ligaments or other suspensory subcutaneous connective tissue structures to temperatures of about 60-90 C, without significant damage to overlying, underlying, or surrounding tissues, are desirable as a noninvasive treatment for sagging. However, it is undesirable to heat the tissue to temperatures greater than about 100 degrees C. or higher, which can cause destructive cavitation (boiling). Unfortunately, previously, no systems or techniques had been developed yet that provide the combination of targeted, precise, local heating to a specified temperature region capable of inducing desired shrinkage of suspensory connective tissues underlying skin and subcutaneous fat.

Figure 2:
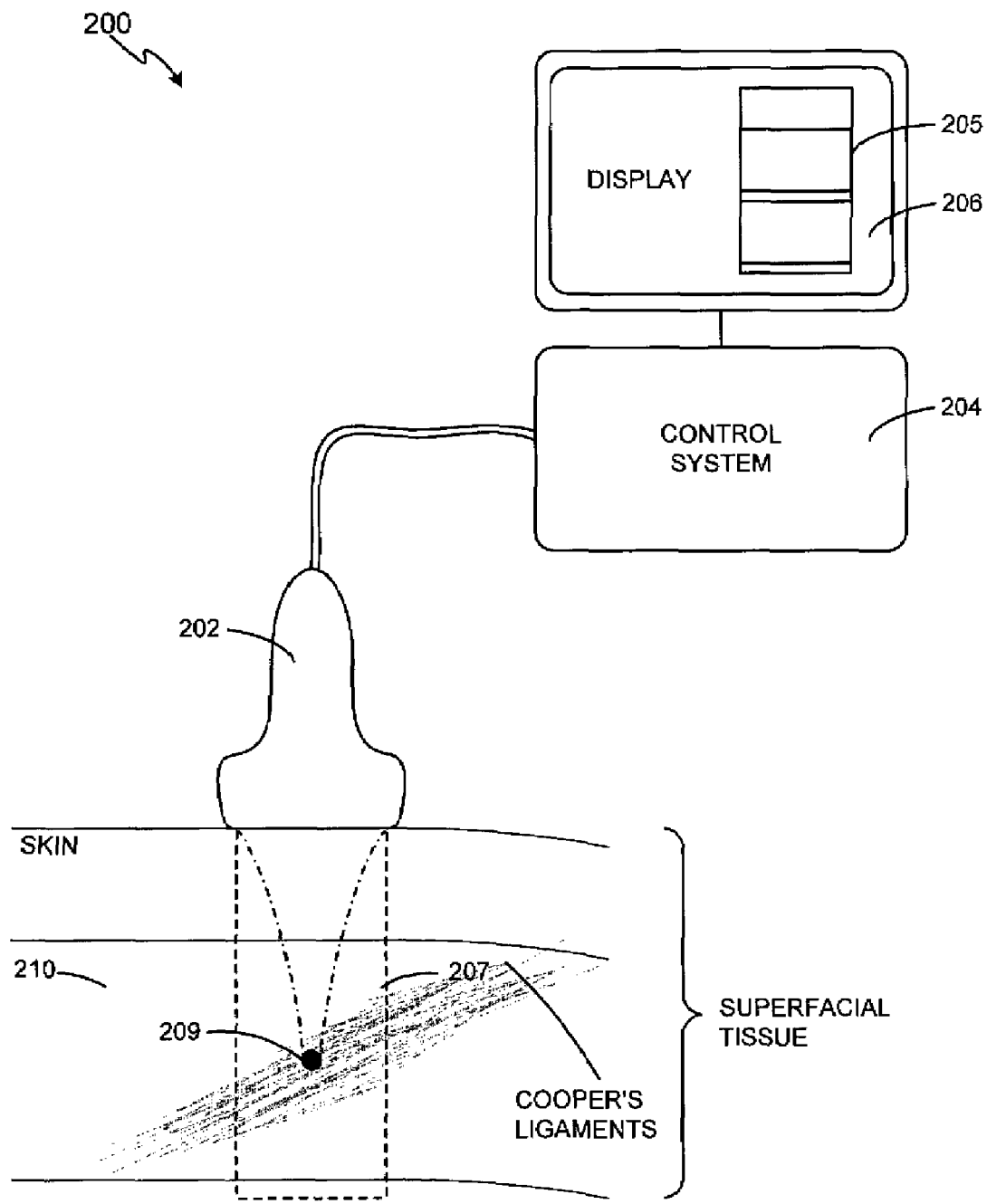
FIG. 2 illustrates a cross sectional diagram of an exemplary probe system in accordance with exemplary embodiments of the present invention.

An exemplary non-invasive mastopexy system overcomes this issues and provides the combination of targeted, precise, local heating to a specified temperature region capable of inducing desired shrinkage of suspensory connective tissues underlying skin and subcutaneous fat. For example, with reference to an exemplary embodiment illustrated in FIG. 2, a non-invasive mastopexy system 200 can comprise a therapy transducer system 202, a control system 204 and a display 206 to provide treatment to a region of interest (ROI) 210. Exemplary transducer system 200 is configured for first, imaging and display of region of interest 210 for localization of the treatment area and surrounding structures, second, delivery of focused, unfocused, or defocused ultrasound energy at a depth, distribution, timing, and energy level to achieve the desired therapeutic effect of thermal ablation to treat cellulite, and third to monitor the treatment area and surrounding structures before, during, and after therapy to plan and assess the results and/or provide feedback to control system 204 and/or an operator.

Transducer probe 202 may be configured in a probe arrangement to provide treatment. Transducer probe 202 may also be configured with various mechanical devices to allow for optimal treatment and therapy, for example to provide controlled positioning of ultrasound therapy transducer 202, such as through a non-invasive configuration and through control by control system 204. Further, transducer probe 202 may also be configured for one-dimensional, two-dimensional, and/or annular arrays, and/or for three-dimensional treatment applications such as that described herein.

Exemplary transducer probe 202 can be configured to be suitably controlled and/or operated in various manners. For example, transducer probe 202 may be configured for use within an ultrasound treatment system, an ultrasound imaging system, an ultrasound monitoring system, and/or any combination of an ultrasound treatment, imaging and/or monitoring system including motion control subsystems.

Control system 204 can be configured with one or more subsystems, processors, input devices, displays and/or the like. Display 206 may be configured to image and/or monitor ROI 210 and/or any particular sub-region within ROI 210. Display 206 can be configured for two-dimensional, three-dimensional, real-time, analog, digital and/or any other type of imaging. Exemplary embodiments of both control system 204 and display 206 are described in greater detail herein.

Region of tissue 210 can comprise a superficial layer, such as, for example the epidermis and/or dermis, subcutaneous fat, Cooper ligaments, and/or muscle. Because Cooper's ligaments are typically about 1 mm to 4 cm deep ROI 210 may comprise an extended area of interest. Also, because Cooper's ligaments vary in depth and thickness at different locations, transducer system 200 is configured to facilitate imaging and treatment at different tissue depths and locations.

That is, exemplary transducer system 200, can be configured to provide cross-sectional two-dimensional imaging of a region 207, displayed as an image 205, with a controlled thermal lesion 209, confined within ROI 210. For example, through such spatial and/or temporal control, an exemplary treatment system 200 can enable the regions of thermal injury to possess arbitrary shape and size and allow the tissue to be treated in a controlled manner.

In accordance with an exemplary embodiment, transducer probe 202 can comprise a variable depth transducer including a transduction element having a piezoelectrically active layer, matching layers and/or other materials for generating radiation or acoustical energy. In other words, transducer probe 202 may be configured to operate at moderate frequencies to provide variable depth treatment within ROI 210. Moreover, transducer probe 202 can also be configured as a multi-directional transducer. Various configurations of transducer probe 202 are described in detail herein.

Exemplary ultrasound transducer probe 202 can be configured in various manners to provide various functions. In one embodiment, transducer probe 202 can be configured for generating high acoustic power for treatment purposes, while also providing for good imaging capabilities. For example, to allow for the treatment spot size to be optimally controlled at various treatment depths, an exemplary embodiment of the present invention may comprise a transducer configured into an array of sub-elements, each sub-element configured for processing acoustic waves with a sufficient bandwidth for good axial resolution.

For example, an ultrasound therapy transducer system can be configured for spatial control and/or temporal control by changing the position of transducer, its drive frequency, focal depth, drive amplitude, and timing of the exemplary transducer. In accordance with various exemplary embodiments, transducer probe 202 can be configured for spatial control, such as by changing the distance from transducer probe 202 to a reflecting surface, or changing the angles of energy focused or unfocused to tissue regions 205 and/or 207, and/or configured for temporal control, such as by controlling changes in the frequency, drive amplitude and timing of transducer probe 202 through control system 204. As a result, changes in the location of the treatment region, the shape and size and/or volume of the spot or region of interest, as well as the thermal conditions, can be dynamically controlled versus time.

In addition to the spatial control, control system 204 and/or transducer probe 202 can also be configured for temporal control, such as through adjustment and optimization of drive amplitude levels, frequency/waveform selections, and timing sequences and other energy drive characteristics to control the treatment of tissue. The spatial and/or temporal control can also be facilitated through open-loop and closed-loop feedback arrangements, such as through the monitoring of various positional and temporal characteristics.

In accordance with another exemplary embodiment of the present invention, control system 204 and/or transducer probe 202 can also be configured for generating high acoustic power for treatment purposes, while also providing for good imaging capabilities. For example, to allow for the treatment spot size to be optimally controlled at various treatment depths, an exemplary embodiment of the present invention may comprise a transducer configured into an array of sub-elements, each sub-element configured for processing acoustic waves with a sufficient bandwidth for good axial resolution such as described in U.S. application Ser. No. 10/944,500, SYSTEM AND METHOD FOR VARIABLE DEPTH ULTRASOUND TREATMENT, filed Sep., 16, 2004, having at least one common inventor, and hereby incorporated by reference.

In accordance with another aspect of the present invention, exemplary ultrasound therapy treatment system 200 may also be configured to provide therapeutic heating, cooling and/or imaging of a treatment region as well as acoustically monitoring the temperature profile or other tissue parameter monitoring of the treatment region and the general vicinity thereof. For example, in accordance with an exemplary embodiment, ultrasound therapy treatment system 200 may be configured with a dynamic feedback arrangement based on monitoring of temperature or other tissue parameters, and/or based on imaging information to suitably adjust the spatial and/or temporal characteristics of the ultrasound therapy transducer.

In order to facilitate imaging, monitoring, treatment and/or temperature control in ROI 210, control system 204 can be configured with various components and devices. For example, Transducer probe 202 can be configured to provide cross sectional two-dimensional imaging of a region 207, for example as displayed in an image 205 within a display 206, as well as generate a controlled thermal lesion 209, confined proximately to Cooper ligaments and the top of the muscle. Therapeutic ultrasound system 200 can be configured to spare the intervening tissue that contains vital structures, as well as tissue posterior to conformal lesion 209.

Figure 3A:
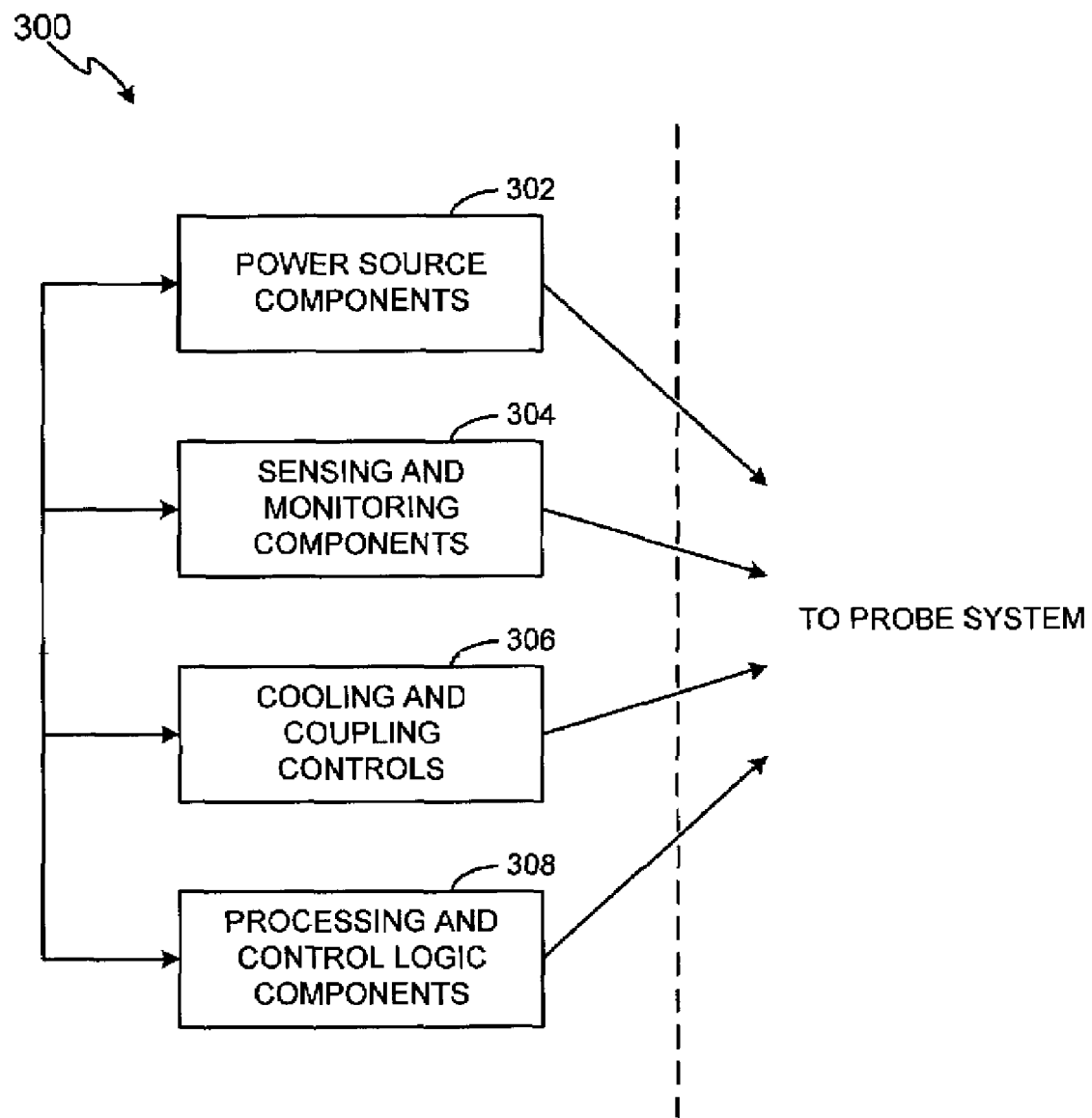
FIGS. 3A and 3B illustrate block diagrams of an exemplary control system in accordance with exemplary embodiments of the present invention.
Figure 3B:
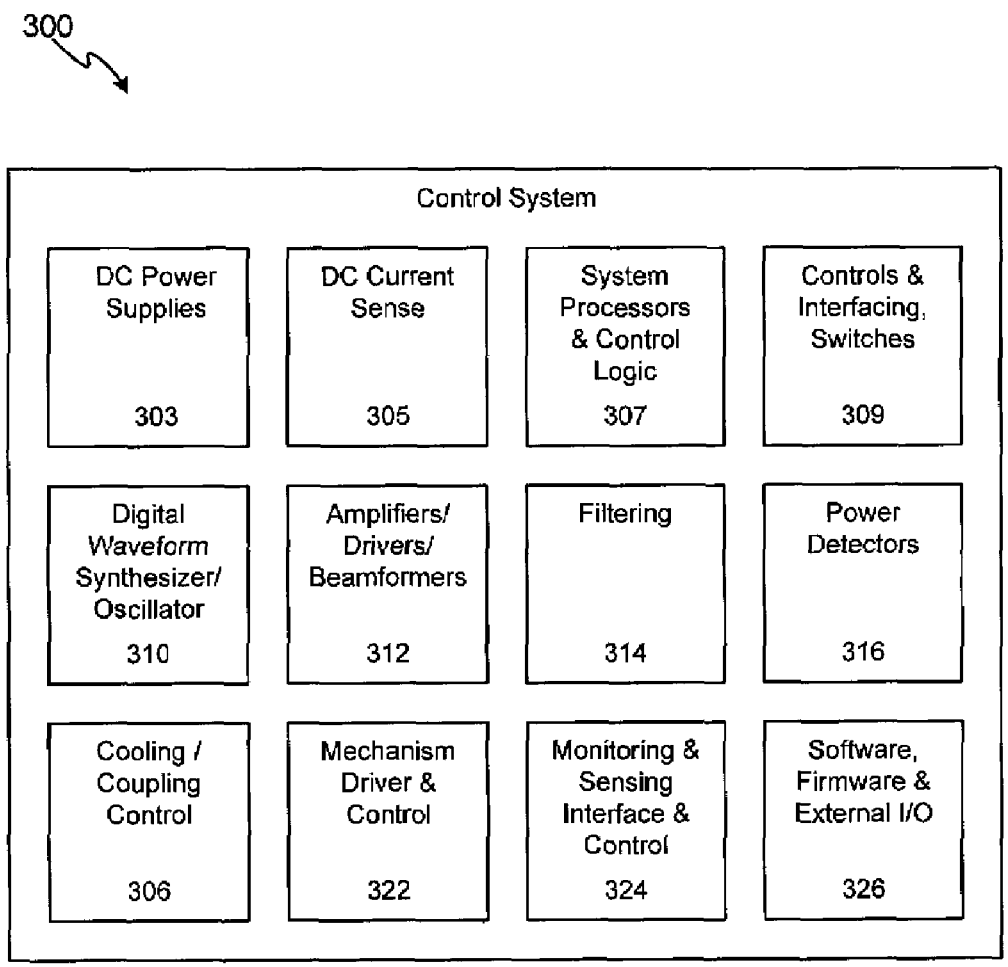

As previously described, control systems 102 and 204 may be configured in various manners with various subsystems and subcomponents. With reference to FIGS. 3A and 3B, in accordance with exemplary embodiments, an exemplary control system 300 can be configured for coordination and control of the entire therapeutic treatment process in accordance with the adjustable settings made by a therapeutic treatment system user. For example, control system 300 can suitably comprise power source components 302, sensing and monitoring components 304, cooling and coupling controls 306, and/or processing and control logic components 308. Control system 300 can be configured and optimized in a variety of ways with more or less subsystems and components to implement the therapeutic system for noninvasive mastopexy, and the embodiment in FIGS. 3A and 3B are merely for illustration purposes.

For example, for power sourcing components 302, control system 300 can comprise one or more direct current (DC) power supplies 303 configured to provide electrical energy for entire control system 300, including power required by a transducer electronic amplifier/driver 312. A DC current sense device 305 can also be provided to confirm the level of power going into amplifiers/drivers 312 for safety and monitoring purposes.

Amplifiers/drivers 312 can comprise multi-channel or single channel power amplifiers and/or drivers. In accordance with an exemplary embodiment for transducer array configurations, amplifiers/drivers 312 can also be configured with a beamformer to facilitate array focusing. An exemplary beamformer can be electrically excited by an oscillator/digitally controlled waveform synthesizer 310 with related switching logic.

The power sourcing components can also include various filtering configurations 314. For example, switchable harmonic filters and/or matching may be used at the output of amplifier/driver 312 to increase the drive efficiency and effectiveness. Power detection components 316 may also be included to confirm appropriate operation and calibration. For example, electric power and other energy detection components 316 may be used to monitor the amount of power going to an exemplary probe system.

Various sensing and monitoring components 304 may also be suitably implemented within control system 300. For example, in accordance with an exemplary embodiment, monitoring, sensing and interface control components 324 may be configured to operate with various motion detection systems implemented within transducer probe 104 to receive and process information such as acoustic or other spatial and temporal information from a region of interest. Sensing and monitoring components can also include various controls, interfacing and switches 309 and/or power detectors 316.

Such sensing and monitoring components 304 can facilitate open-loop and/or closed-loop feedback systems within treatment system 100.

For example, in such an open-loop system, a system user can suitably monitor the imaging and or other spatial or temporal parameters and then adjust or modify same to accomplish a particular treatment objective. Instead of, or in combination with open-loop feedback configurations, an exemplary treatment system can comprise a closed-loop feedback system, wherein images and/or spatial/temporal parameters can be suitably monitored within monitoring component to generate signals.

During operation of exemplary treatment system 100, a lesion configuration of a selected size, shape, orientation is determined. Based on that lesion configuration, one or more spatial parameters are selected, along with suitable temporal parameters, the combination of which yields the desired conformal lesion. Operation of the transducer can then be initiated to provide the conformal lesion or lesions. Open and/or closed-loop feedback systems can also be implemented to monitor the spatial and/or temporal characteristics, and/or other tissue parameter monitoring, to further control the conformal lesions.

Cooling/coupling control systems 306 may be provided to remove waste heat from exemplary probe 104, provide a controlled temperature at the superficial tissue interface and deeper into tissue, and/or provide acoustic coupling from transducer probe 104 to region-of-interest 106. Such cooling/coupling control systems 306 can also be configured to operate in both open-loop and/or closed-loop feedback arrangements with various coupling and feedback components.

Processing and control logic components 308 can comprise various system processors and digital control logic 307, such as one or more of microcontrollers, microprocessors, field-programmable gate arrays (FPGAs), computer boards, and associated components, including firmware and control software 326, which interfaces to user controls and interfacing circuits as well as input/output circuits and systems for communications, displays, interfacing, storage, documentation, and other useful functions. System software and firmware 326 controls all initialization, timing, level setting, monitoring, safety monitoring, and all other system functions required to accomplish user-defined treatment objectives. Further, various control switches 308 can also be suitably configured to control operation.

An exemplary transducer probe 104 can also be configured in various manners and comprise a number of reusable and/or disposable components and parts in various embodiments to facilitate its operation. For example, transducer probe 104 can be configured within any type of transducer probe housing or arrangement for facilitating the coupling of transducer to a tissue interface, with such housing comprising various shapes, contours and configurations depending on the particular treatment application. For example, in accordance with an exemplary embodiment, transducer probe 104 can be depressed against a tissue interface whereby blood perfusion is partially or wholly cut-off, and tissue flattened in superficial treatment region-of-interest 106. Transducer probe 104 can comprise any type of matching, such as for example, electric matching, which may be electrically switchable; multiplexer circuits and/or aperture/element selection circuits; and/or probe identification devices, to certify probe handle, electric matching, transducer usage history and calibration, such as one or more serial EEPROM (memories). Transducer probe 104 may also comprise cables and connectors; motion mechanisms, motion sensors and encoders; thermal monitoring sensors; and/or user control and status related switches, and indicators such as LEDs. For example, a motion mechanism in probe 104 may be used to controllably create multiple lesions, or sensing of probe motion itself may be used to controllably create multiple lesions and/or stop creation of lesions, e.g. for safety reasons if probe 104 is suddenly jerked or is dropped. In addition, an external motion encoder arm may be used to hold the probe during use, whereby the spatial position and attitude of probe 104 is sent to the control system to help controllably create lesions. Furthermore, other sensing functionality such as profilometers or other imaging modalities may be integrated into the probe in accordance with various exemplary embodiments.

Figure 4A:
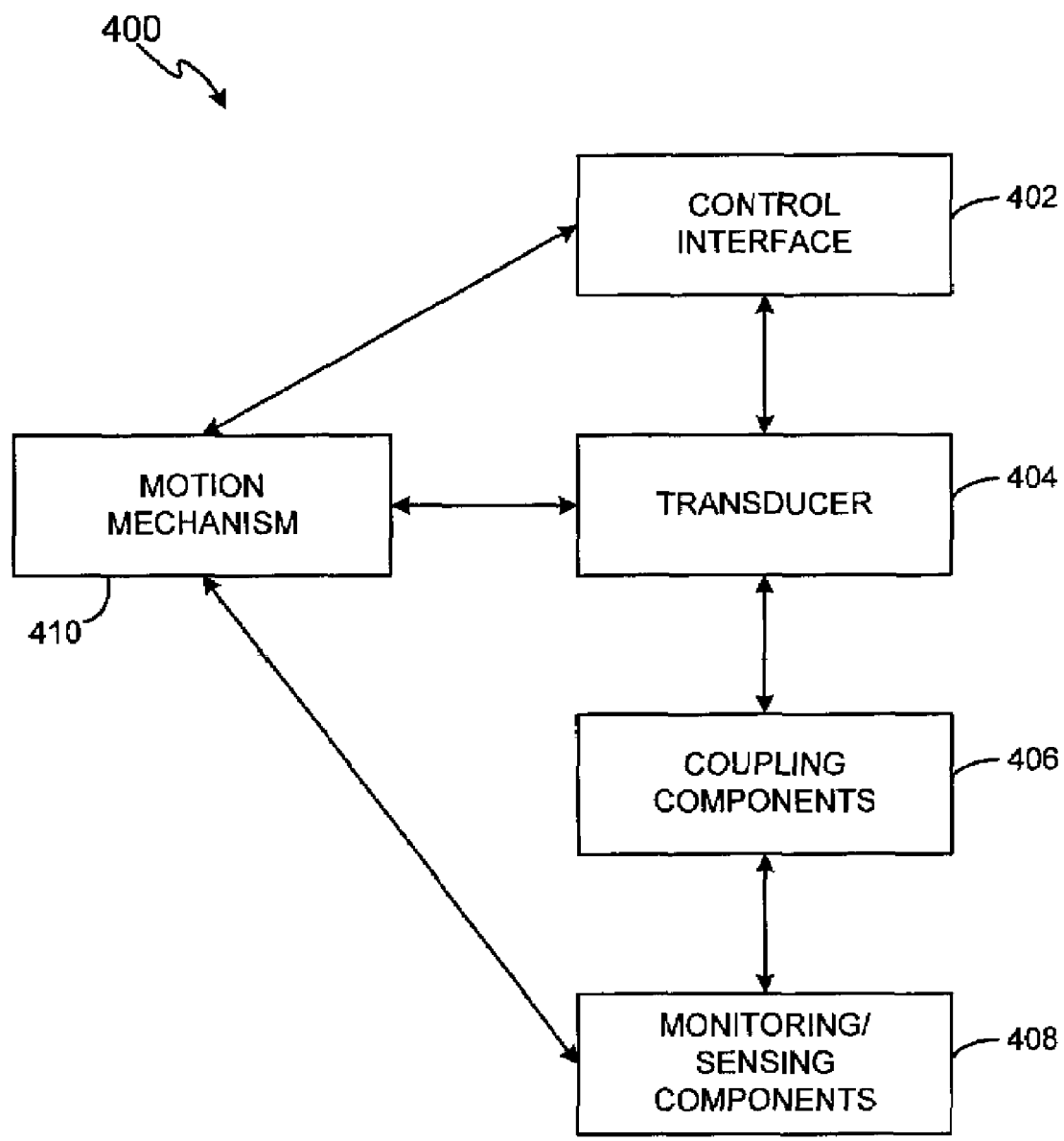
FIGS. 4A and 4B illustrate block diagrams of an exemplary probe system in accordance with exemplary embodiments of the present invention.
Figure 4B:
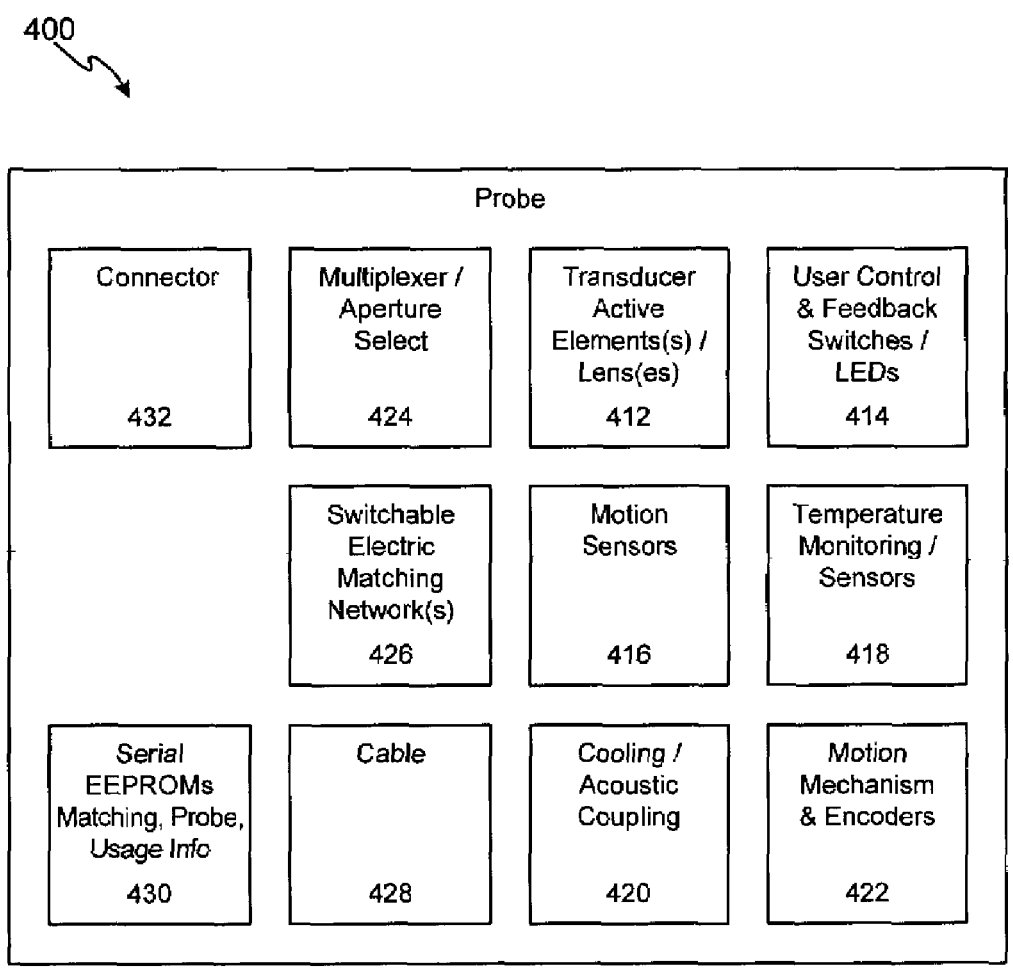

With reference to FIGS. 4A and 4B, in accordance with an exemplary embodiment, a transducer probe 400 can comprise a control interface 402, a transducer 404, coupling components 406, and monitoring/sensing components 408, and/or motion mechanism 410. However, transducer probe 400 can be configured and optimized in a variety of ways with more or less parts and components to provide ultrasound energy for noninvasive mastopexy, and the embodiment in FIGS. 4A and 4B are merely for illustration purposes.

In accordance with an exemplary embodiment of the present invention, transducer probe 400 is configured to deliver energy over varying temporal and/or spatial distributions in order to provide energy effects and initiate responses in a region of interest. These effects can include, for example, thermal, cavitational, hydrodynamic, and resonance induced tissue effects. For example, exemplary transducer probe 400 can be operated under one or more frequency ranges to provide two or more energy effects and initiate one or more responses in the region of interest. In addition, transducer probe 400 can also be configured to deliver planar, defocused and/or focused energy to a region of interest to provide two or more energy effects and to initiate one or more reactions. These responses can include, for example, diathermy, hemostasis, revascularization, angiogenesis, growth of interconnective tissue, tissue reformation, ablation of existing tissue, protein synthesis and/or enhanced cell permeability. These and various other exemplary embodiments for such combined ultrasound treatment, effects and responses are more fully set forth in U.S. patent application Ser. No. 10/950,112, entitled "METHOD AND SYSTEM FOR COMBINED ULTRASOUND TREATMENT," Filed Sep. 24, 2004 and incorporated herein by reference.

Control interface 402 is configured for interfacing with control system 300 to facilitate control of transducer probe 400. Control interface components 402 can comprise multiplexer/aperture select 424, switchable electric matching networks 426, serial EEPROMs and/or other processing components and matching and probe usage information 430 and interface connectors 432.

Coupling components 406 can comprise various devices to facilitate coupling of transducer probe 400 to a region of interest. For example, coupling components 406 can comprise cooling and acoustic coupling system 420 configured for acoustic coupling of ultrasound energy and signals. Acoustic cooling/coupling system 420 with possible connections such as manifolds may be utilized to couple sound into the region-of-interest, control temperature at the interface and deeper into tissue, provide liquid-filled lens focusing, and/or to remove transducer waste heat. Coupling system 420 may facilitate such coupling through use of various coupling mediums, including air and other gases, water and other fluids, gels, solids, and/or any combination thereof, or any other medium that allows for signals to be transmitted between transducer active elements 412 and a region of interest. In addition to providing a coupling function, in accordance with an exemplary embodiment, coupling system 420 can also be configured for providing temperature control during the treatment application. For example, coupling system 420 can be configured for controlled cooling of an interface surface or region between transducer probe 400 and a region of interest and beyond and beyond by suitably controlling the temperature of the coupling medium. The suitable temperature for such coupling medium can be achieved in various manners, and utilize various feedback systems, such as thermocouples, thermistors or any other device or system configured for temperature measurement of a coupling medium. Such controlled cooling can be configured to further facilitate spatial and/or thermal energy control of transducer probe 400.

Figure 11:
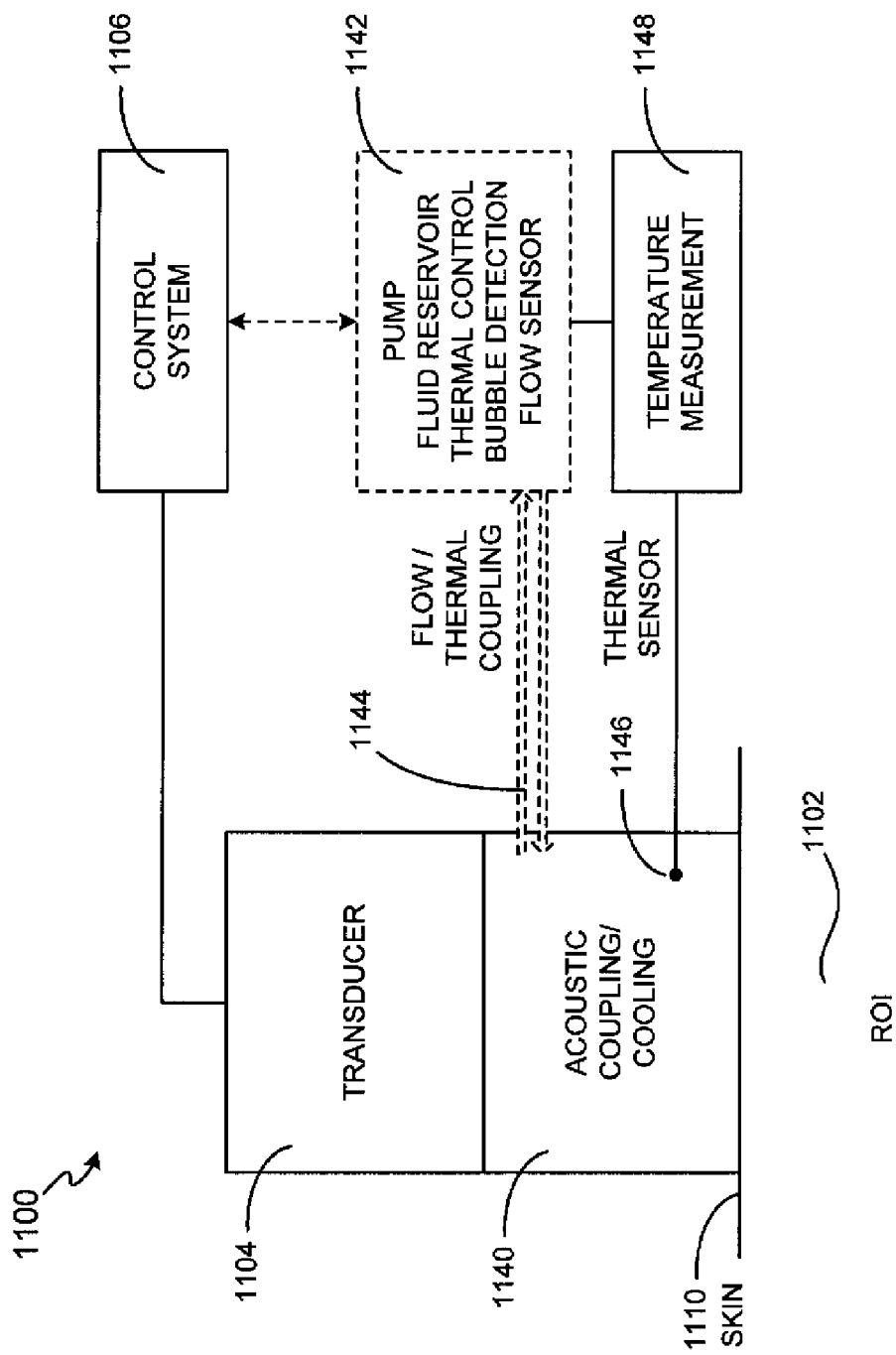
FIG. 11 illustrates a schematic diagram of an acoustic coupling and cooling system in accordance with an exemplary embodiment of the present invention.

In accordance with an exemplary embodiment, with additional reference to FIG. 11, acoustic coupling and cooling 1140 can be provided to acoustically couple energy and imaging signals from transducer probe 1104 to and from the region of interest 1102, to provide thermal control at the probe to region-of-interest interface 1110 and deeper into tissue, and to remove potential waste heat from the transducer probe at region 1144. Temperature monitoring can be provided at the coupling interface via a thermal sensor 1146 to provide a mechanism of temperature measurement 1148 and control via control system 1106 and a thermal control system 1142. Thermal control may consist of passive cooling such as via heat sinks or natural conduction and convection or via active cooling such as with peltier thermoelectric coolers, refrigerants, or fluid-based systems comprised of pump, fluid reservoir, bubble detection, flow sensor, flow channels/tubing 1144 and thermal control 1142.

Monitoring and sensing components 408 can comprise various motion and/or position sensors 416, temperature monitoring sensors 418, user control and feedback switches 414 and other like components for facilitating control by control system 300, e.g., to facilitate spatial and/or temporal control through open-loop and closed-loop feedback arrangements that monitor various spatial and temporal characteristics.

Motion mechanism 410 can comprise manual operation, mechanical arrangements, or some combination thereof. For example, a motion mechanism 422 can be suitably controlled by control system 300, such as through the use of accelerometers, positions of transducer probe 400. Linear, rotational or variable movement can be facilitated, e.g., those depending on the treatment application and tissue contour surface.

Transducer 404 can comprise one or more transducers configured for producing conformal lesions of thermal injury in superficial human tissue within a region of interest through precise spatial and temporal control of acoustic energy deposition. Transducer 404 can also comprise one or more transduction elements and/or lenses 412. The transduction elements can comprise a piezoelectrically active material, such as lead zirconante titanate (PZT), or any other piezoelectrically active material, such as a piezoelectric ceramic, crystal, plastic, and/or composite materials, as well as lithium niobate, lead titanate, barium titanate, and/or lead metaniobate. In addition to, or instead of, a piezoelectrically active material, transducer 404 can comprise any other materials configured for generating radiation and/or acoustical energy. Transducer 404 can also comprise one or more matching layers configured along with the transduction element such as coupled to the piezoelectrically active material. Acoustic matching layers and/or damping may be employed as necessary to achieve the desired electroacoustic response.

In accordance with an exemplary embodiment, the thickness of the transduction element of transducer 404 can be configured to be uniform. That is, a transduction element 412 can be configured to have a thickness that is substantially the same throughout. In accordance with another exemplary embodiment, the thickness of a transduction element 412 can also be configured to be variable. For example, transduction element(s) 412 of transducer 404 can be configured to have a first thickness selected to provide a center operating frequency of a lower range, for example from approximately 1 MHz to 5 MHz. Transduction element 404 can also be configured with a second thickness selected to provide a center operating frequency of a higher range, for example from approximately 5 MHz to 15 MHz or more. Transducer 404 can be configured as a single broadband transducer excited with at least two or more frequencies to provide an adequate output for generating a desired response. Transducer 404 can also be configured as two or more individual transducers, wherein each transducer comprises one or more transduction element. The thickness of the transduction elements can be configured to provide center-operating frequencies in a desired treatment range. For example, transducer 404 can comprise a first transducer configured with a first transduction element having a thickness corresponding to a center frequency range of approximately 1 MHz to 5 MHz, and a second transducer configured with a second transduction element having a thickness corresponding to a center frequency of approximately 5 MHz to 15 MHz or more.

Figure 5:
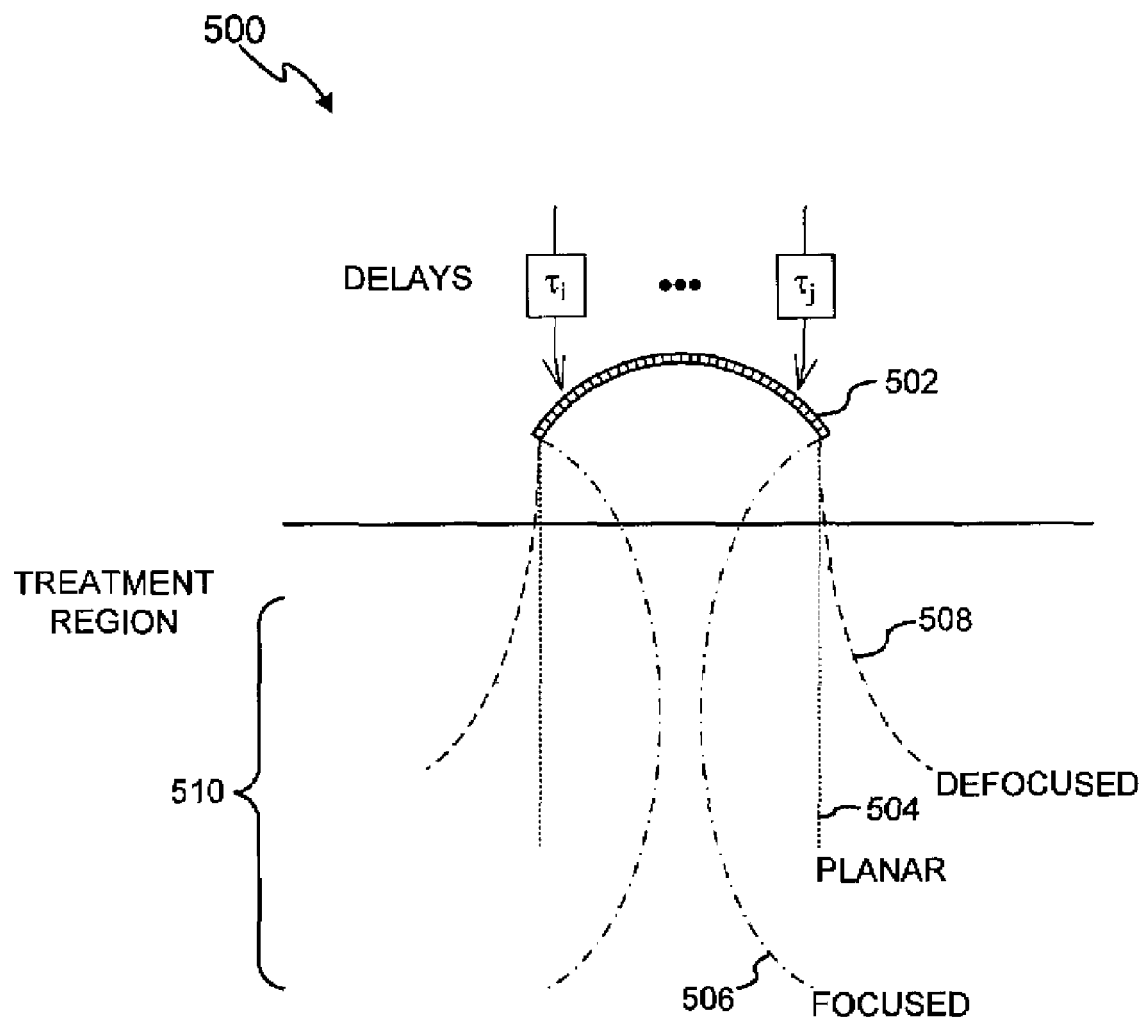
FIG. 5 illustrates a cross-sectional diagram of an exemplary transducer in accordance with an exemplary embodiment of the present invention.

Transducer 404 may be composed of one or more individual transducers in any combination of focused, planar, or unfocused single-element, multi-element, or array transducers, including 1-D, 2-D, and annular arrays; linear, curvilinear, sector, or spherical arrays; spherically, cylindrically, and/or electronically focused, defocused, and/or lensed sources. For example, with reference to an exemplary embodiment depicted in FIG. 5, transducer 500 can be configured as an acoustic array 502 to facilitate phase focusing. That is, transducer 500 can be configured as an array of electronic apertures that may be operated by a variety of phases via variable electronic time delays. By the term "operated," the electronic apertures of transducer 500 may be manipulated, driven, used, and/or configured to produce and/or deliver an energy beam corresponding to the phase variation caused by the electronic time delay. For example, these phase variations can be used to deliver defocused beams 508, planar beams 504, and/or focused beams 506, each of which may be used in combination to achieve different physiological effects in a region of interest 510. Transducer 500 may additionally comprise any software and/or other hardware for generating, producing and or driving a phased aperture array with one or more electronic time delays.

Transducer 500 can also be configured to provide focused treatment to one or more regions of interest using various frequencies. In order to provide focused treatment, transducer 500 can be configured with one or more variable depth devices to facilitate treatment. For example, transducer 500 may be configured with variable depth devices disclosed in U.S. patent application Ser. No. 10/944,500, entitled "System and Method for Variable Depth Ultrasound", filed on Sep. 16, 2004, having at least one common inventor and a common Assignee as the present application, and incorporated herein by reference. In addition, transducer 500 can also be configured to treat one or more additional ROI 510 through the enabling of sub-harmonics or pulse-echo imaging, as disclosed in U.S. patent application Ser. No. 10/944,499, entitled "Method and System for Ultrasound Treatment with a Multi-directional Transducer", filed on Sep. 16, 2004, having at least one common inventor and a common Assignee as the present application, and also incorporated herein by reference.

Moreover, any variety of mechanical lenses or variable focus lenses, e.g. liquid-filled lenses, may also be used to focus and or defocus the sound field. For example, with reference to exemplary embodiments depicted in FIGS. 6A and 6B, transducer 600 may also be configured with an electronic focusing array 604 in combination with one or more transduction elements 606 to facilitate increased flexibility in treating ROI 610. Array 604 may be configured in a manner similar to transducer 502. That is, array 604 can be configured as an array of electronic apertures that may be operated by a variety of phases via variable electronic time delays, for example, $T_1, T_2 \ldots T_j$. By the term "operated," the electronic apertures of array 604 may be manipulated, driven, used, and/or configured to produce and/or deliver energy in a manner corresponding to the phase variation caused by the electronic time delay. For example, these phase variations can be used to deliver defocused beams, planar beams, and/or focused beams, each of which may be used in combination to achieve different physiological effects in ROI 610.

Transduction elements 606 may be configured to be concave, convex, and/or planar. For example, in an exemplary embodiment depicted in FIG. 6A, transduction elements 606 are configured to be concave in order to provide focused energy for treatment of ROI 610. Additional embodiments are disclosed in U.S. patent application Ser. No. 10/944,500, entitled "Variable Depth Transducer System and Method", and again incorporated herein by reference.

Figure 6A:
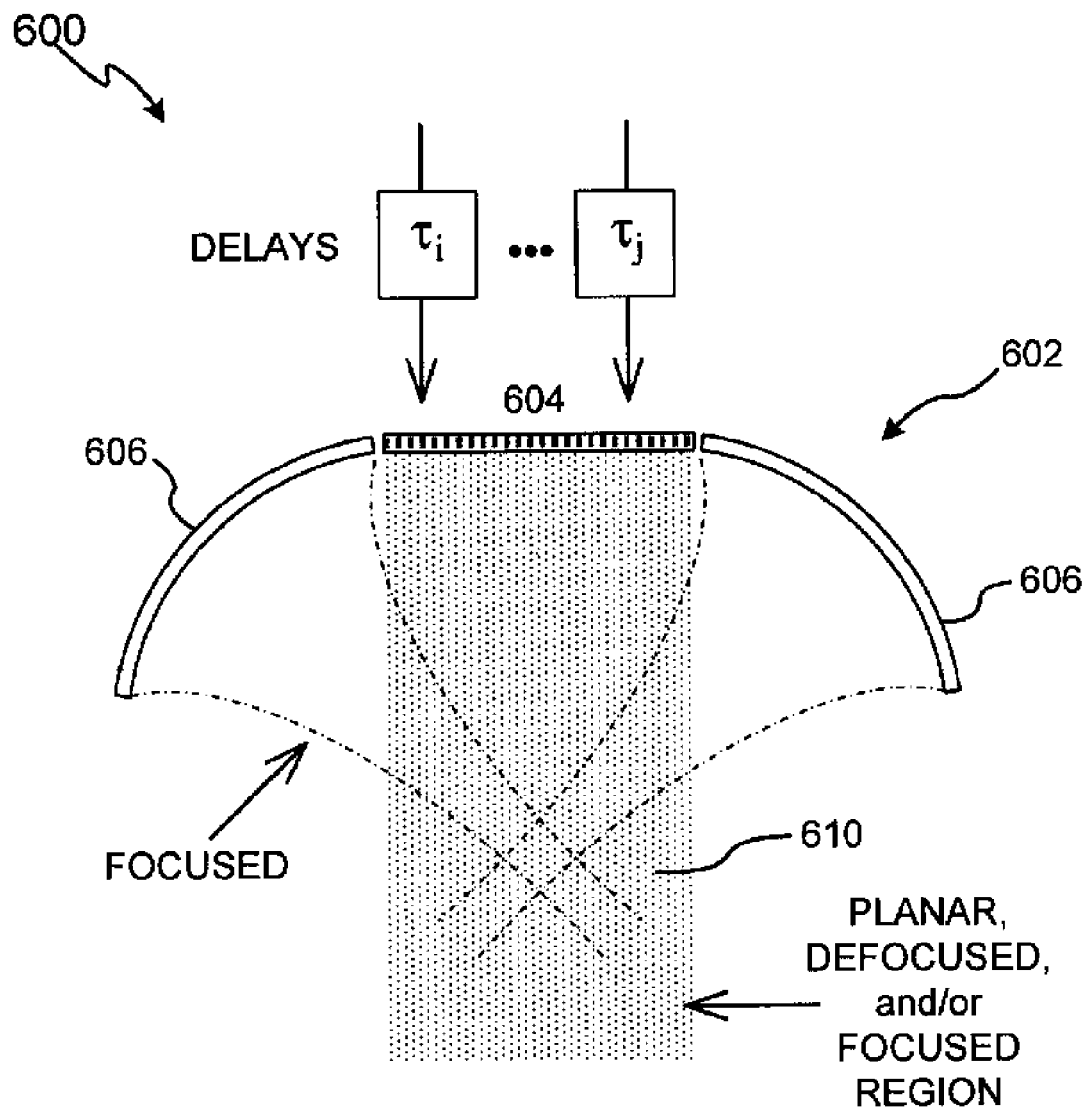
FIGS. 6A and 6B illustrate cross-sectional diagrams of an exemplary transducer in accordance with exemplary embodiments of the present invention.
Figure 6B:
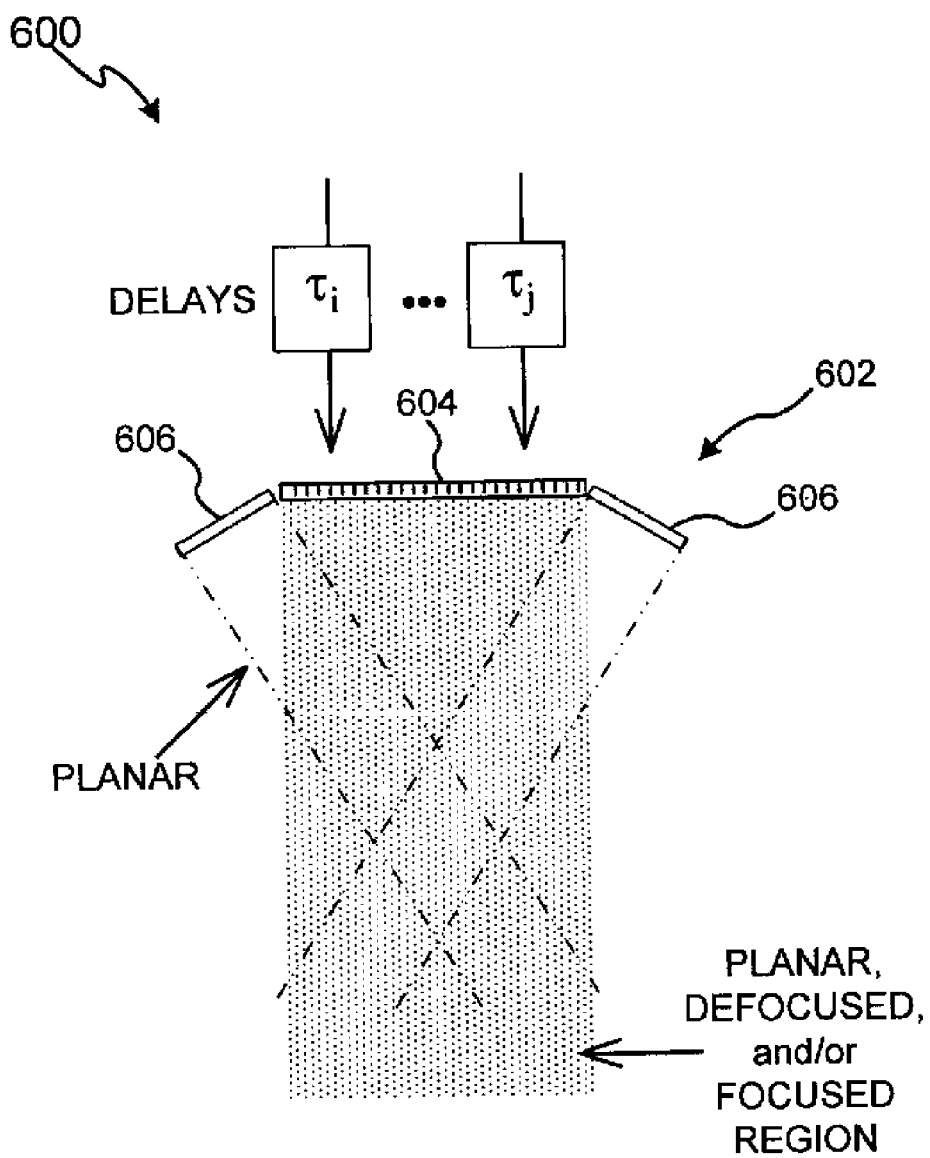

In another exemplary embodiment, depicted in FIG. 6B, transduction elements 606 can be configured to be substantially flat in order to provide substantially uniform energy to ROI 610. While FIGS. 6A and 6B depict exemplary embodiments with transduction elements 604 configured as concave and substantially flat, respectively, transduction elements 604 can be configured to be concave, convex, and/or substantially flat. In addition, transduction elements 604 can be configured to be any combination of concave, convex, and/or substantially flat structures. For example, a first transduction element can be configured to be concave, while a second transduction element can be configured to be substantially flat.

Figure 8A:
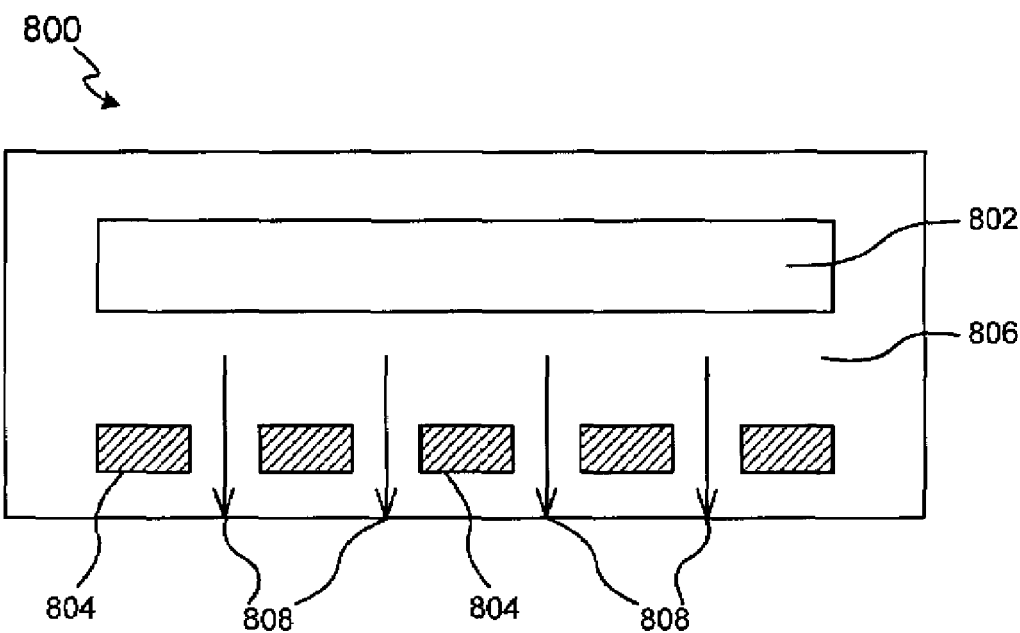
FIGS. 8A and 8B illustrate cross-sectional diagrams of an exemplary transducer in accordance with another exemplary embodiment of the present invention.
Figure 8B:
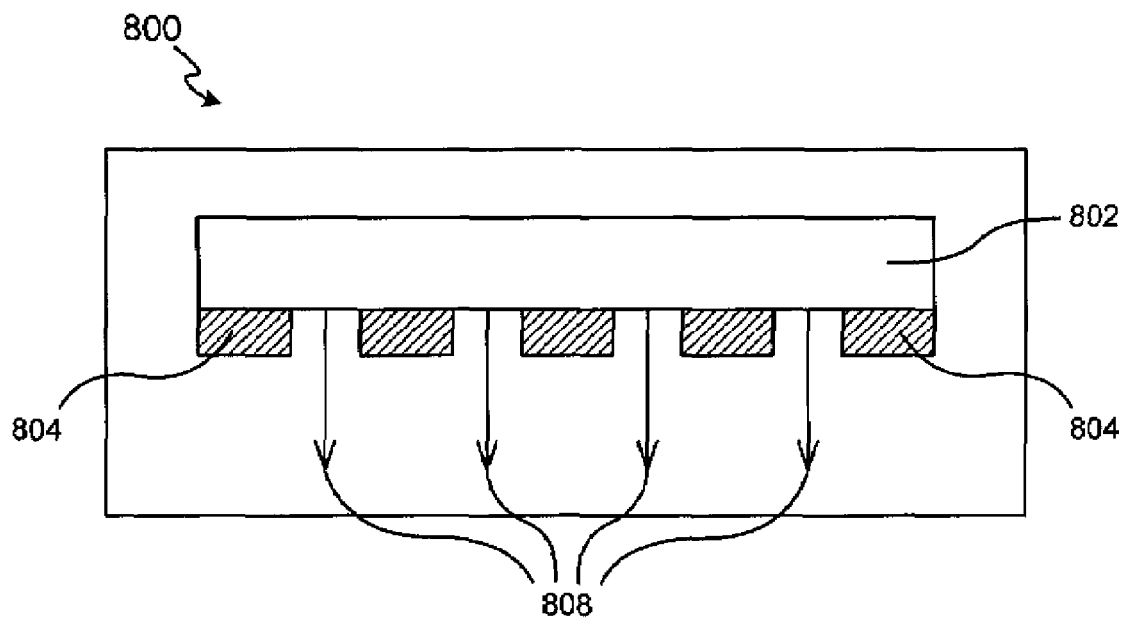

With reference to FIGS. 8A and 8B, transducer 404 can be configured as single-element arrays, wherein a single-element 802, e.g., a transduction element of various structures and materials, can be configured with a plurality of masks 804, such masks comprising ceramic, metal or any other material or structure for masking or altering energy distribution from element 802, creating an array of energy distributions 808. Masks 804 can be coupled directly to element 802 or separated by a standoff 806, such as any suitably solid or liquid material.

Figure 10A:
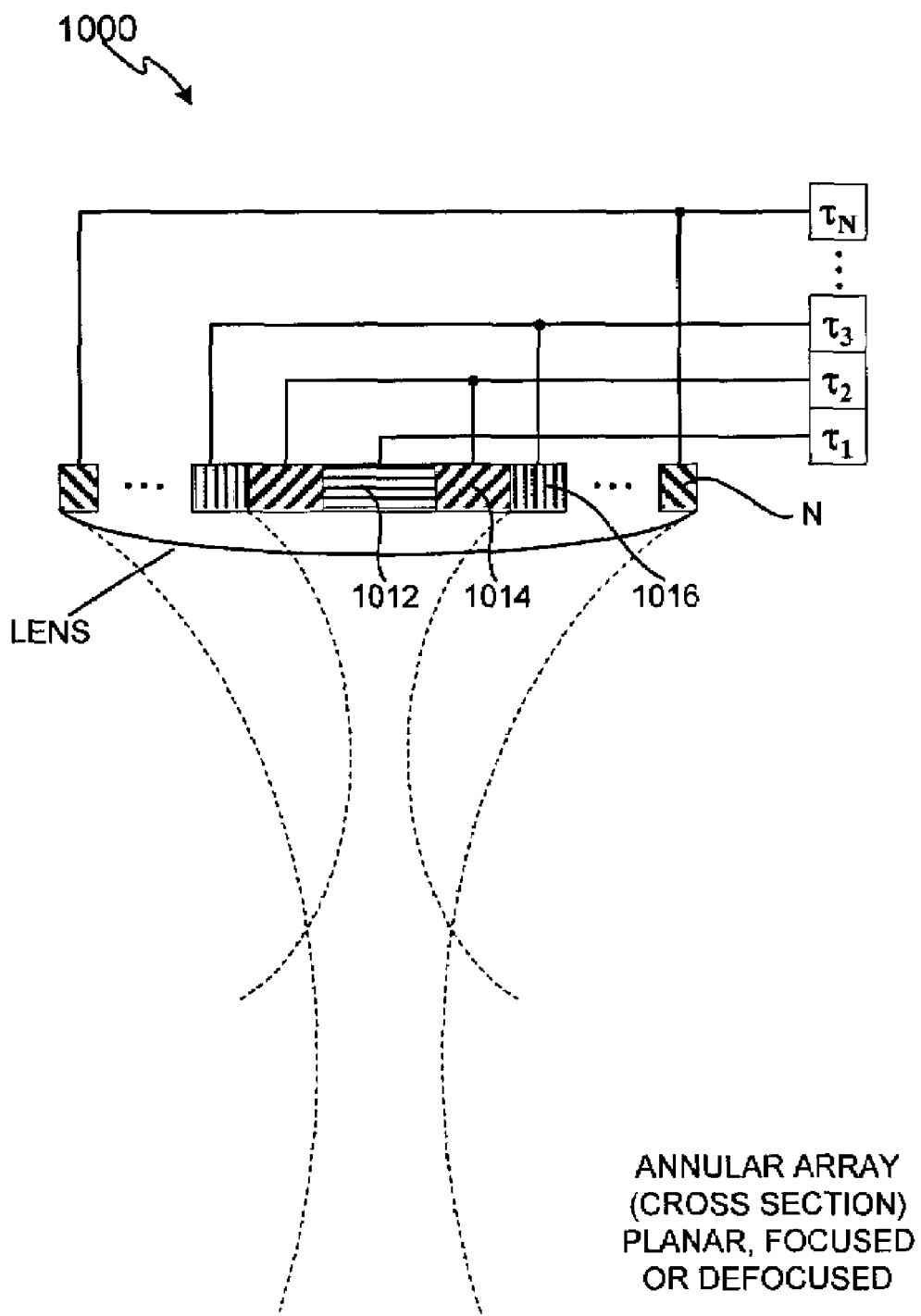
FIGS. 10A-10F illustrate cross-sectional diagrams of exemplary transducers in accordance with other exemplary embodiments of the present invention.
Figure 10B:
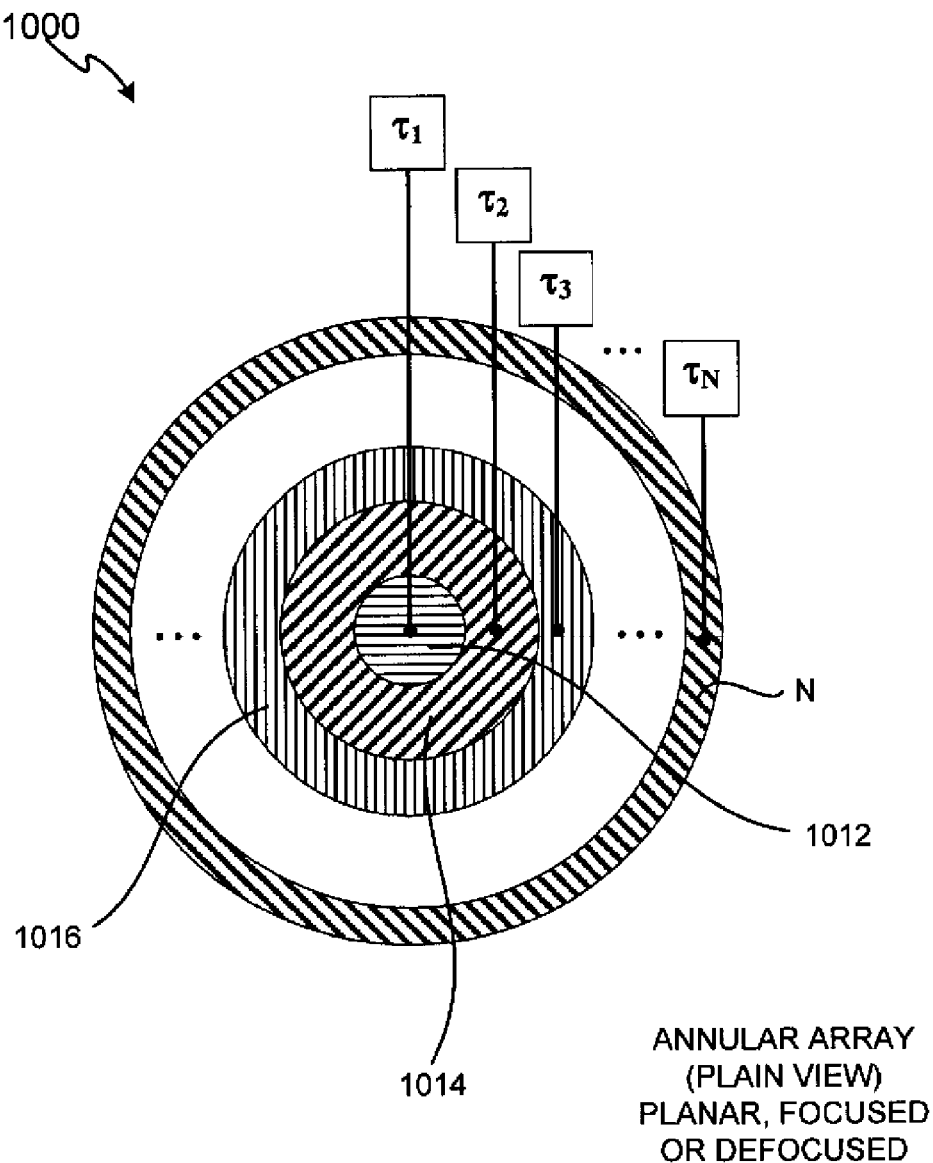
Figure 10C:
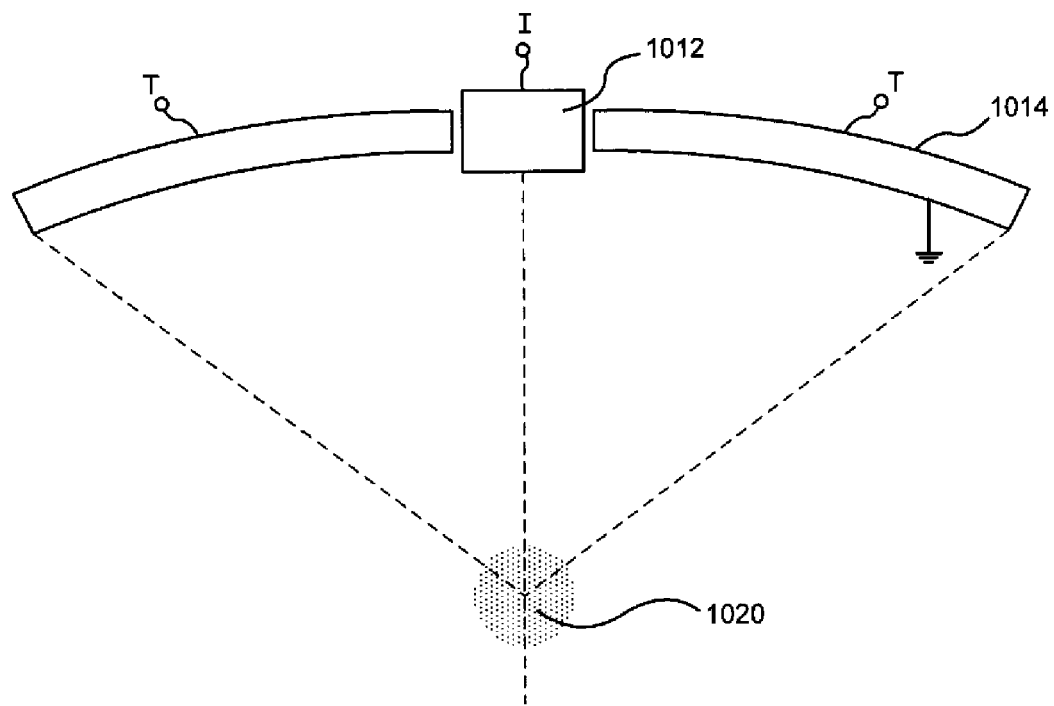
Figure 10D:
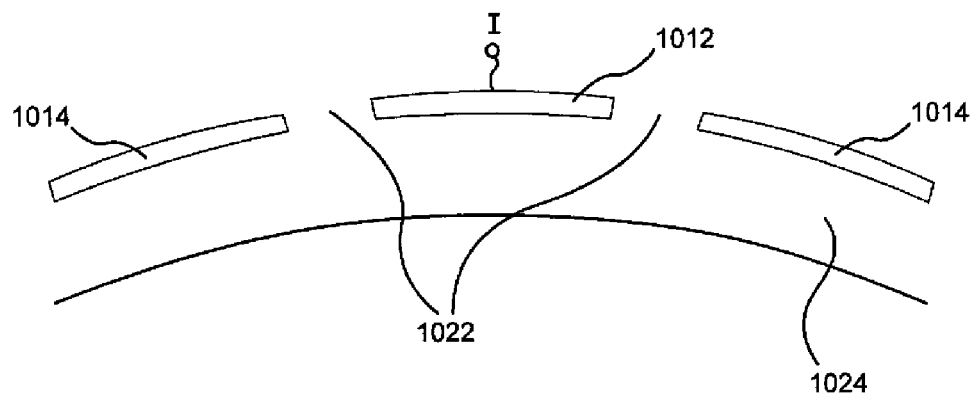
Figure 10E:
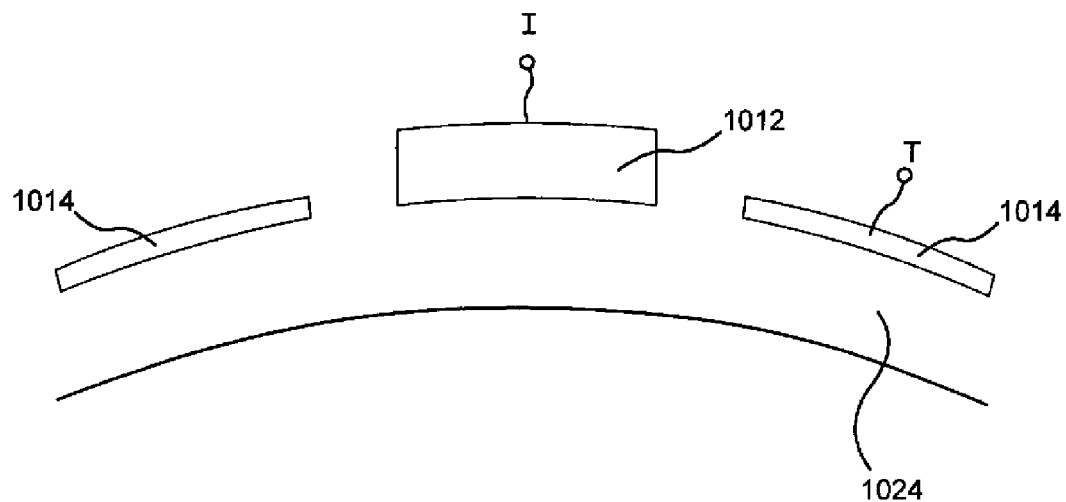

An exemplary transducer 404 can also be configured as an annular array to provide planar, focused and/or defocused acoustical energy. For example, with reference to FIGS. 10A and 10B, in accordance with an exemplary embodiment, an annular array 1000 can comprise a plurality of rings 1012, 1014, 1016 to N. Rings 1012, 1014, 1016 to N can be mechanically and electrically isolated into a set of individual elements, and can create planar, focused, or defocused waves. For example, such waves can be centered on-axis, such as by methods of adjusting corresponding transmit and/or receive delays, $T_1, T_2, T_3 \ldots T_N$. An electronic focus can be suitably moved along various depth positions, and can enable variable strength or beam tightness, while an electronic defocus can have varying amounts of defocusing. In accordance with an exemplary embodiment, a lens and/or convex or concave shaped annular array 1000 can also be provided to aid focusing or defocusing such that any time differential delays can be reduced. Movement of annular array 1000 in one, two or three-dimensions, or along any path, such as through use of probes and/or any conventional robotic arm mechanisms, may be implemented to scan and/or treat a volume or any corresponding space within a region of interest.

Figure 10F:
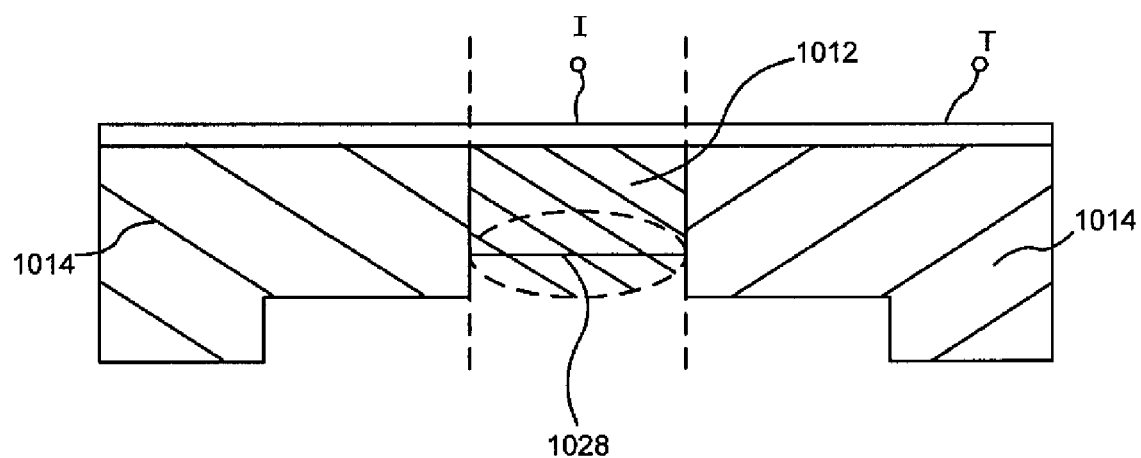

Transducer 404 can also be configured in other annular or non-array configurations for imaging/therapy functions. For example, with reference to FIGS. 10C-10F, a transducer can comprise an imaging element 1012 configured with therapy element(s) 1014. Elements 1012 and 1014 can comprise a single-transduction element, e.g., a combined imaging/transducer element, or separate elements, can be electrically isolated 1022 within the same transduction element or between separate imaging and therapy elements, and/or can comprise standoff 1024 or other matching layers, or any combination thereof. For example, with particular reference to FIG. 10F, a transducer can comprise an imaging element 1012 having a surface 1028 configured for focusing, defocusing or planar energy distribution, with therapy elements 1014 including a stepped-configuration lens configured for focusing, defocusing, or planar energy distribution.

In accordance with another aspect of the invention, transducer probe 400 may be configured to provide one, two or three-dimensional treatment applications for focusing acoustic energy to one or more regions of interest. For example, as discussed above, transducer probe 400 can be suitably diced to form a one-dimensional array, e.g., a transducer comprising a single array of sub-transduction elements.

Figure 9:
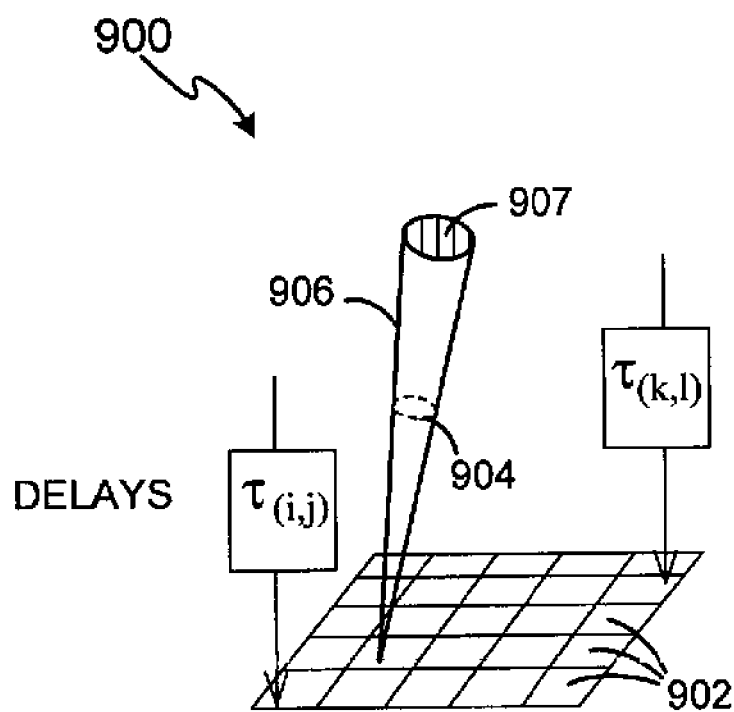
FIG. 9 illustrates an exemplary transducer configured as a two-dimensional array for ultrasound treatment in accordance with an exemplary embodiment of the present invention.

In accordance with another exemplary embodiment, transducer probe 400 may be suitably diced in two-dimensions to form a two-dimensional array. For example, with reference to FIG. 9, an exemplary two-dimensional array 900 can be suitably diced into a plurality of two-dimensional portions 902. Two-dimensional portions 902 can be suitably configured to focus on the treatment region at a certain depth, and thus provide respective slices 904, 907 of the treatment region. As a result, the two-dimensional array 900 can provide a two-dimensional slicing of the image place of a treatment region, thus providing two-dimensional treatment.

In accordance with another exemplary embodiment, transducer probe 400 may be suitably configured to provide three-dimensional treatment. For example, to provide three dimensional treatment of a region of interest, with reference again to FIG. 3, a three-dimensional system can comprise transducer probe 400 configured with an adaptive algorithm, such as, for example, one utilizing three-dimensional graphic software, contained in a control system, such as control system 300. The adaptive algorithm is suitably configured to receive two-dimensional imaging, temperature and/or treatment information relating to the region of interest, process the received information, and then provide corresponding three-dimensional imaging, temperature and/or treatment information.

In accordance with an exemplary embodiment, with reference again to FIG. 9, an exemplary three-dimensional system can comprise a two-dimensional array 900 configured with an adaptive algorithm to suitably receive 904 slices from different image planes of the treatment region, process the received information, and then provide volumetric information 906, e.g., three-dimensional imaging, temperature and/or treatment information. Moreover, after processing the received information with the adaptive algorithm, the two-dimensional array 900 may suitably provide therapeutic heating to the volumetric region 906 as desired.

Alternatively, rather than utilizing an adaptive algorithm, such as three-dimensional software, to provide three-dimensional imaging and/or temperature information, an exemplary three-dimensional system can comprise a single transducer 404 configured within a probe arrangement to operate from various rotational and/or translational positions relative to a target region.

Figure 7:
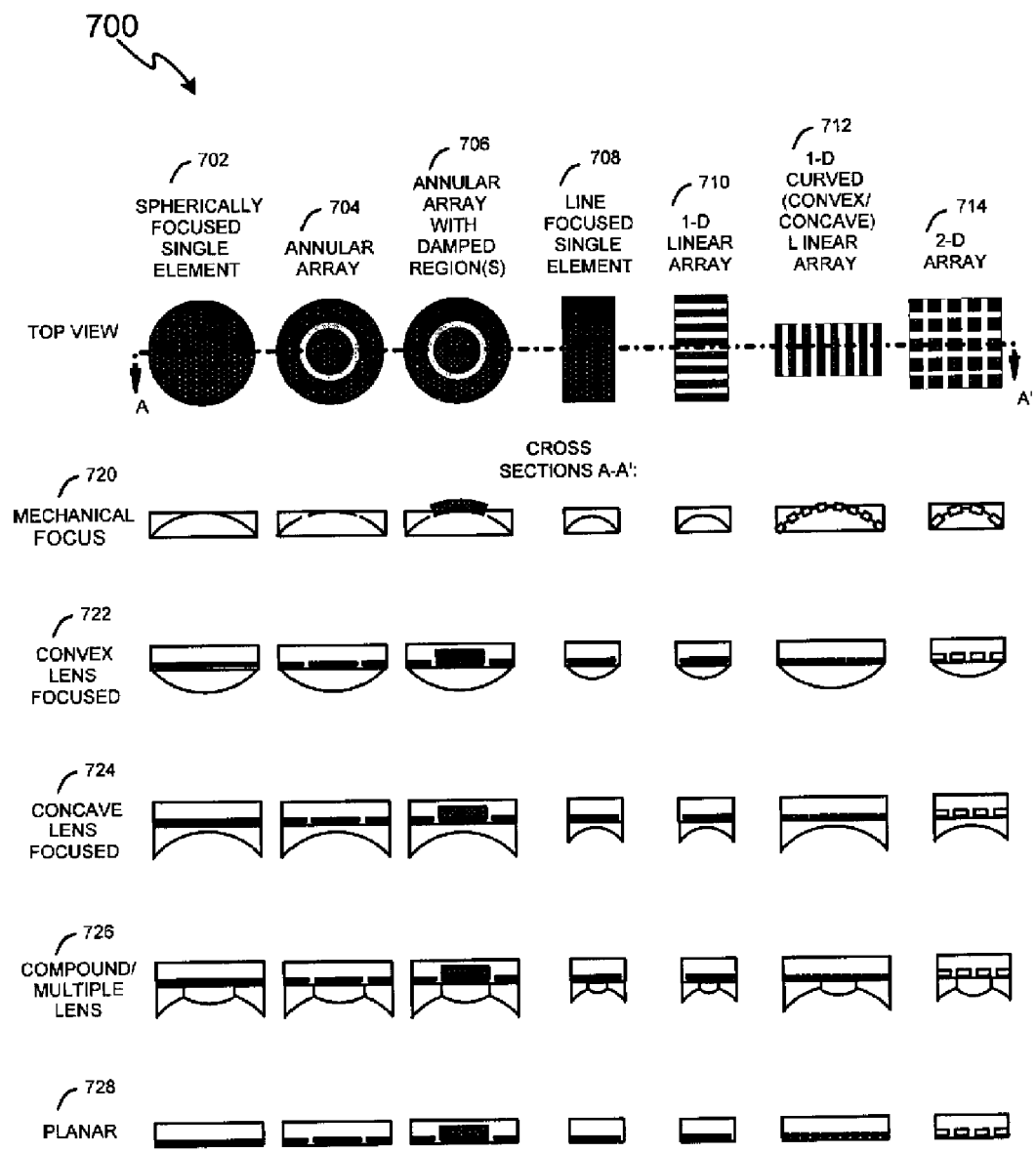
FIG. 7 illustrates exemplary transducer configurations for ultrasound treatment in accordance with various exemplary embodiments of the present invention.

To further illustrate the various structures for transducer 404, with reference to FIG. 7, ultrasound therapy transducer 700 can be configured for a single focus, an array of foci, a locus of foci, a line focus, and/or diffraction patterns. Transducer 700 can also comprise single elements, multiple elements, annular arrays, one-, two-, or three-dimensional arrays, broadband transducers, and/or combinations thereof, with or without lenses, acoustic components, and mechanical and/or electronic focusing. Transducers configured as spherically focused single elements 702, annular arrays 704, annular arrays with damped regions 706, line focused single elements 708, 1-D linear arrays 710, 1-D curvilinear arrays in concave or convex form, with or without elevation focusing, 2-D arrays, and 3-D spatial arrangements of transducers may be used to perform therapy and/or imaging and acoustic monitoring functions. For any transducer configuration, focusing and/or defocusing may be in one plane or two planes via mechanical focus 720, convex lens 722, concave lens 724, compound or multiple lenses 726, planar form 728, or stepped form, such as illustrated in Fig, 10F. Any transducer or combination of transducers may be utilized for treatment. For example, an annular transducer may be used with an outer portion dedicated to therapy and the inner disk dedicated to broadband imaging wherein such imaging transducer and therapy transducer have different acoustic lenses and design, such as illustrated in FIG. 10C-10F.

Various shaped treatment lesions can be produced using the various acoustic lenses and designs in FIGS. 10A-10F. For example, cigar-shaped lesions may be produced from a spherically focused source, and/or planar lesions from a flat source. Concave planar sources and arrays can produce a "V-shaped" or ellipsoidal lesion. Electronic arrays, such as a linear array, can produce defocused, planar, or focused acoustic beams that may be employed to form a wide variety of additional lesion shapes at various depths. An array may be employed alone or in conjunction with one or more planar or focused transducers. Such transducers and arrays in combination produce a very wide range of acoustic fields and their associated benefits. A fixed focus and/or variable focus lens or lenses may be used to further increase treatment flexibility. A convex-shaped lens, with acoustic velocity less than that of superficial tissue, may be utilized, such as a liquid-filled lens, gel-filled or solid gel lens, rubber or composite lens, with adequate power handling capacity; or a concave-shaped, low profile, lens may be utilized and composed of any material or composite with velocity greater than that of tissue. While the structure of transducer source and configuration can facilitate a particular shaped lesion as suggested above, such structures are not limited to those particular shapes as the other spatial parameters, as well as the temporal parameters, can facilitate additional shapes within any transducer structure and source.

Through operation of ultrasound system 100, a method for mastopexy can be realized that can facilitate effective and efficient therapy without creating chronic injury to human tissue. For example, a user may first select one or more transducer probe configurations for treating a region of interest. The user may select any probe configuration described herein. Because the treatment region ranges from approximately 1 mm to 4 cm, exemplary transducer probes may include, for example, an annular array, a variable depth transducer, a mechanically moveable transducer, a cylindrical-shaped transducer, and the like. As used herein, the term user may include a person, employee, doctor, nurse, and/or technician, utilizing any hardware and/or software of other control systems.

Once one or more transducers are selected, the user may then image a region of interest in order to plan a treatment protocol. By imaging a region of interest, the user may user the same treatment transducer probe and/or one or more additional transducers to image the region of interest at a high resolution. In one embodiment, the transducer may be configured to facilitate high speed imaging over a large region of interest to enable accurate imaging over a large region of interest. In another embodiment, ultrasound imaging may include the use of Doppler flow monitoring and/or color flow monitoring. In addition other means of imaging such as photography and other visual optical methods, MRI, X-Ray, PET, infrared or others can be utilized separately or in combination for imaging and feedback of the superficial tissue and the vascular tissue in the region of interest.

Figure 12:
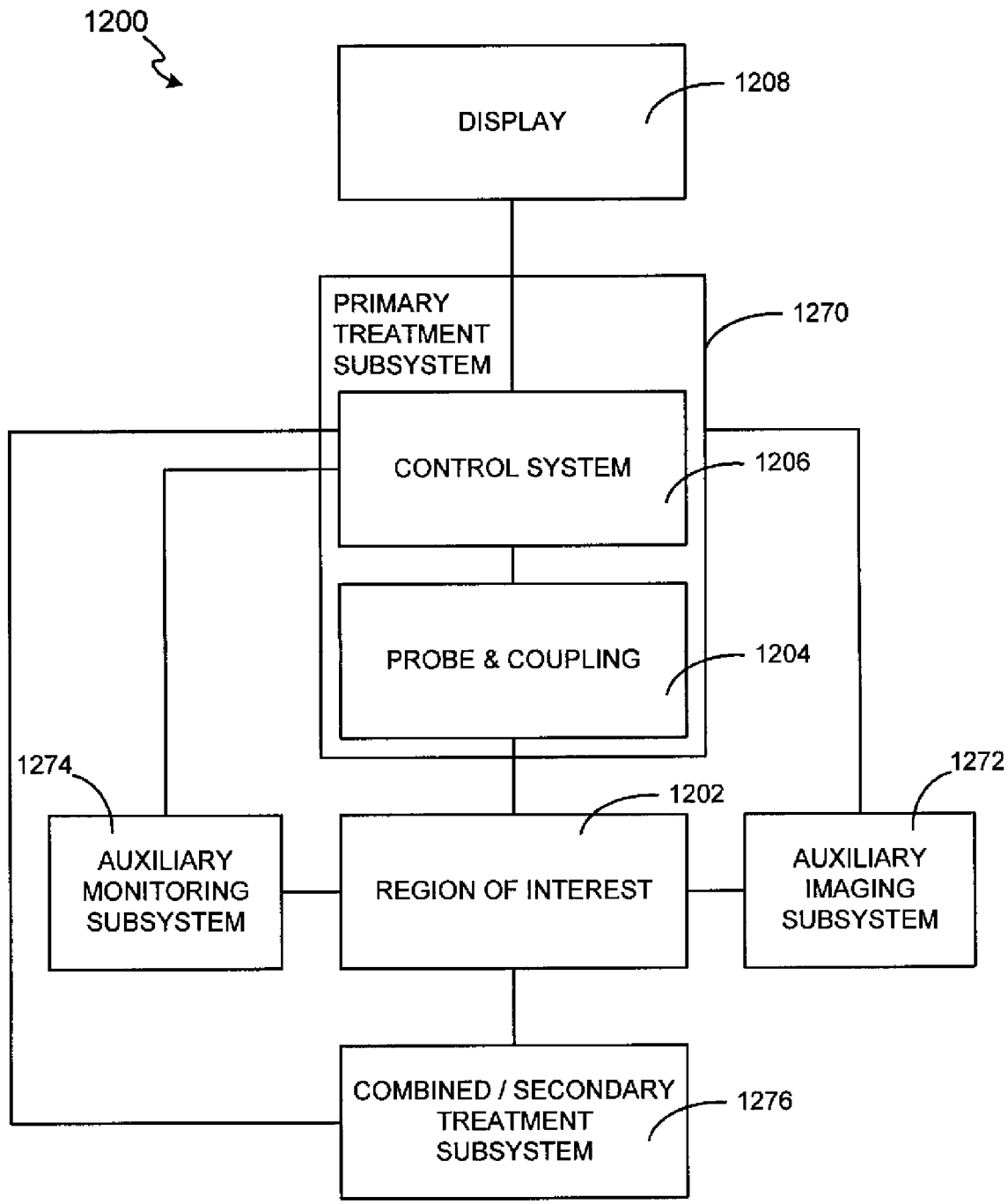
FIG. 12 illustrates a block diagram of a treatment system comprising an ultrasound treatment subsystem combined with additional subsystems and methods of treatment monitoring and/or treatment imaging as well as a secondary treatment subsystem in accordance with an exemplary embodiment of the present invention.

In accordance with another exemplary embodiment, with reference to FIG. 12, an exemplary treatment system 200 can be configured with and/or combined with various auxiliary systems to provide additional functions. For example, an exemplary treatment system 1200 for treating a region of interest 1202 can comprise a control system 1206, a probe 1204, and a display 1208. Treatment system 1200 further comprises an auxiliary imaging modality 1274 and/or auxiliary monitoring modality 1272 may be based upon at least one of photography and other visual optical methods, magnetic resonance imaging (MRI), computed tomography (CT), optical coherence tomography (OCT), electromagnetic, microwave, or radio frequency (RF) methods, positron emission tomography (PET), infrared, ultrasound, acoustic, or any other suitable method of visualization, localization, or monitoring of region-of-interest 1202, including imaging/monitoring enhancements. Such imaging/monitoring enhancement for ultrasound imaging via probe 1204 and control system 1206 could comprise M-mode, persistence, filtering, color, Doppler, and harmonic imaging among others; furthermore an ultrasound treatment system 1270, as a primary source of treatment, may be combined with a secondary source of treatment 1276, including radio frequency (RF), intense pulsed light (IPL), laser, infrared laser, microwave, or any other suitable energy source.

Because the location of Cooper's ligaments varies from one patient to another (due to genetics, weight, age, etc.), high speed imaging using a transducer can facilitate tracking the depth of treatment within a patient, imaging the ligament variations within the chest, and/or determining the length and/or location of one or more Cooper's ligaments within a patient. This imaging/tracking/determining information can also be used to calculate the optimal shrinkage of the Cooper's ligaments needed to facilitate the desired level of mastopexic results.

By planning a treatment protocol, the user may choose one or more spatial and/or temporal characteristics to provide conformal ultrasound energy to a region of interest. For example, the user may select one or more spatial characteristics to control, including, for example, the use one or more transducers, one or more mechanical and/or electronic focusing mechanisms, one or more transduction elements, one or more placement locations of the transducer relative to the region of interest, one or more feedback systems, one or more mechanical arms, one or more orientations of the transducer, one or more temperatures of treatment, one or more coupling mechanisms and/or the like.

In addition, the user may choose one or more temporal characteristics to control in order to facilitate treatment of the region of interest. For example, the user may select and/or vary the treatment time, frequency, power, energy, amplitude and/or the like in order to facilitate temporal control. For more information on selecting and controlling ultrasound spatial and temporal characteristics, see U.S. application Ser. No. 11/163,148, entitled "Method and System for Controlled Thermal Injury," filed Oct. 6, 2005 and incorporated herein by reference.

After planning of a treatment protocol is complete, the treatment protocol can be implemented. That is, a transducer system of the present invention can be used to deliver ultrasound energy to a treatment region to ablate select tissue in order to facilitate mastopexy. By delivering energy, the transducer may be driven at a select frequency, a phased array may be driven with certain temporal and/or spatial distributions, a transducer may be configured with one or more transduction elements to provide focused, defocused and/or planar energy, and/or the transducer may be configured and/or driven in any other ways hereinafter devised.

In one exemplary embodiment, energy is delivered in relatively small ablative areas in order to minimize and/or prevent scar tissue from forming. That is, each ablative area of treatment can range from approximately sub-millimeter to several millimeters in size.

In one exemplary embodiment, energy is delivered at a treatment depth of approximately 1 mm to 4 cm. The energy may range from 1 MHz to about 15 MHz, with typical applications ranging from 2 MHz to 8 MHz. In order to deliver energy in this treatment range, the transducer can be driven at power levels ranging from 10 W to 150 W or more. Because of the high power and focused treatment that the transducer provides, treatment times for a region of interest can range from 20 milliseconds to 2000 milliseconds or more. Because treatment time and treatment power are interrelated, these variables may differ from one patient to another and/or from one region of interest to another.

Once the treatment protocol has been implemented, the region of tissue may have one or more responses in reaction to the treatment. For example, in one embodiment, the tissue responds by causing additional contraction of the Cooper's ligaments and/or other treatment tissues.

Upon treatment, the steps outlined above can be repeated one or more additional times to provide for optimal treatment results. Different ablation sizes and shapes may affect the recovery time and time between treatments. For example, in general, the larger the surface area of the treatment lesion, the faster the recovery. The series of treatments can also enable the user to tailor additional treatments in response to a patient's responses to the ultrasound treatment.

The present invention has been described above with reference to various exemplary embodiments. However, those skilled in the art will recognize that changes and modifications may be made to the exemplary embodiments without departing from the scope of the present invention. For example, the various operational steps, as well as the components for carrying out the operational steps, may be implemented in alternate ways depending upon the particular application or in consideration of any number of cost functions associated with the operation of the system, e.g., various steps may be deleted, modified, or combined with other steps. These and other changes or modifications are intended to be included within the scope of the present invention, as set forth in the following claims.

What is claimed is:

1. A method for noninvasive mastopexy, said method comprising:
    selecting a probe configuration based on a spatial and a temporal parameter;
    imaging with ultrasound a treatment region of a breast, said treatment region comprising a Cooper's ligament;
    verifying said temporal and said spatial parameters of said probe;
    coupling of said probe to said treatment region; and
    applying ultrasound energy from said probe to ablate a portion of said treatment region to facilitate mastopexy; and
    modifying a shape of said breast.

2. The method of claim 1, wherein said step of applying ultrasound energy includes applying conformal ultrasound energy in the range of about 1 MHz to about 15 MHz.

3. The method of claim 1, wherein said step of applying ultrasound energy includes applying conformal ultrasound energy in the range of about 2 MHz to about 8 MHz.

4. The method of claim 1, further comprising a step of re-imaging said treatment region to confirm ablation of said portion of said treatment region.

5. The method of claim 1, further comprising applying ultrasound energy from said probe to ablate a second portion of said treatment region.

6. A method for providing noninvasive mastopexy, said method comprising:
    imaging with ultrasound a region of interest of a breast comprising a ligament;
    delivering ultrasound energy from a transducer probe to said region of interest comprising said ligament;
    ablating said ligament in said region of interest with said ultrasound energy; and
    monitoring for a modified shape of said breast.

7. The method of claim 6, wherein said ligament is a Cooper's ligament.

8. The method of claim 6, wherein said step of delivering ultrasound energy includes applying conformal ultrasound energy in the range of about 1 MHz to about 15 MHz.

9. The method of claim 6, wherein said step of delivering ultrasound energy includes applying conformal ultrasound energy in the range of about 2 MHz to about 8 MHz.

10. The method of claim 6 further comprising a step of re-imaging said region of interest to confirm ablation of said ligament.

11. The method of claim 6 further comprising applying ultrasound energy to ablate a second ligament in said region of interest.

12. A method for providing noninvasive ultrasound mastopexy treatment, the method comprising:
    imaging a treatment area in a breast and below a skin surface, said treatment area comprising a muscle and a ligament connected to a portion of breast tissue;
    targeting at least a portion of said treatment area;
    delivering ultrasound energy to said at least a portion of said treatment area at specified depth below said skin surface;
    coagulating at least a portion of said muscle and said ligament connected to said portion of breast tissue with said ultrasound energy and thereby lifting said breast.

13. The method of claim 12, wherein said step of delivering ultrasound energy includes applying conformal ultrasound energy in the range of about 1 MHz to about 15 MHz.

14. The method of claim 12, wherein said step of delivering ultrasound energy includes applying conformal ultrasound energy in the range of about 2 MHz to about 8 MHz.

15. The method of claim 12 further comprising a step of re-imaging said region of interest to confirm ablation of said ligament.

16. The method of claim 12, further comprising applying ultrasound energy to coagulate a second ligament in said region of interest.

17. The method of claim 12, further comprising applying ultrasound energy to coagulate a second portion of said muscle in said region of interest.

* * * * *